United States Patent
Seiki et al.

(10) Patent No.: US 11,422,126 B2
(45) Date of Patent: Aug. 23, 2022

(54) CANCER EXAMINATION METHOD AND EXAMINATION KIT

(71) Applicant: The University of Tokyo, Tokyo (JP)

(72) Inventors: Motoharu Seiki, Tokyo (JP); Naohiko Koshikawa, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 744 days.

(21) Appl. No.: 16/103,833

(22) Filed: Aug. 14, 2018

(65) Prior Publication Data
US 2019/0064149 A1     Feb. 28, 2019

Related U.S. Application Data

(62) Division of application No. 14/763,481, filed as application No. PCT/JP2014/053355 on Feb. 13, 2014, now abandoned.

(30) Foreign Application Priority Data

Feb. 13, 2013  (JP) ................... 2013-026026
Oct. 1, 2013   (JP) ................... 2013-206511

(51) Int. Cl.
    *G01N 33/574*   (2006.01)
    *G01N 33/50*    (2006.01)
    *C12N 15/113*   (2010.01)
    *C07K 14/715*   (2006.01)
    *A61K 31/713*   (2006.01)
    *C07K 16/28*    (2006.01)
    *C07K 16/30*    (2006.01)

(52) U.S. Cl.
    CPC ........ *G01N 33/5011* (2013.01); *A61K 31/713* (2013.01); *C07K 14/715* (2013.01); *C07K 16/2866* (2013.01); *C07K 16/30* (2013.01); *C12N 15/113* (2013.01); *C12N 15/1137* (2013.01); *G01N 33/5023* (2013.01); *G01N 33/574* (2013.01); *C12N 2310/14* (2013.01); *G01N 2333/912* (2013.01); *G01N 2500/04* (2013.01); *G01N 2500/10* (2013.01)

(58) Field of Classification Search
CPC combination set(s) only.
See application file for complete search history.

(56) References Cited

U.S. PATENT DOCUMENTS

| 8,183,357 B2 * | 5/2012 | Mather | A61K 47/6897 |
| | | | 536/23.53 |
| 2008/0241067 A1 | 10/2008 | Zimmerman et al. | |
| 2010/0183618 A1 | 7/2010 | Hasegawa et al. | |
| 2011/0281279 A1 * | 11/2011 | Hamer | G01N 33/573 |
| | | | 435/7.4 |

OTHER PUBLICATIONS

Beauchamp et al., "Ephs and Ephrins in Cancer: Ephrin-A1 Signaling", *Semin Cell Dev Biol.*, Author Manuscript, Feb. 2012 (13 pages).
Manish et al., "Emerging strategies for EphA2 receptor targeting for cancer therapeutics", *Expert Opin Ther Targets*, Author Manuscript, Jan. 2011 (31 pages).
Pasquale, Elena, "Eph receptors and ephrins in cancer: bidirectional signaling and beyond", *Nature Reviews/Cancer*, vol. 10, Mar. 2010, pp. 165-180.
Poincloux, Renaud et al., "Matrix invasion by tumor cells: a focus on MT1-MMP trafficking to invadopodia", *Journal of Cell Science* 122, pp. 3015-3024, Sep. 1, 2009.
Seiki, Motoharu et al., "Role of pericellular proteolysis by membrane-type 1 matrix metalloproteinase in cancer invasion and angiogenesis", *Cancer and Metastasis Review* 22: pp. 129-143, 2003.

* cited by examiner

*Primary Examiner* — Mark Halvorson
(74) *Attorney, Agent, or Firm* — Squire Patton Boggs (US) LLP

(57) ABSTRACT

An object of the present invention is to elucidate a molecular mechanism of ligand-independent activation of EphA2 in cancer cells, make EphA2 a more useful target in the treatment of cancer, and provide a cancer testing method and the like using the mechanism. The present invention provides, for example, a cancer testing method including a step of measuring an amount of an EphA2 protein fragment having a molecular weight of from 30 kDa to 80 kDa in a sample derived from a subject.

4 Claims, 36 Drawing Sheets

Specification includes a Sequence Listing.

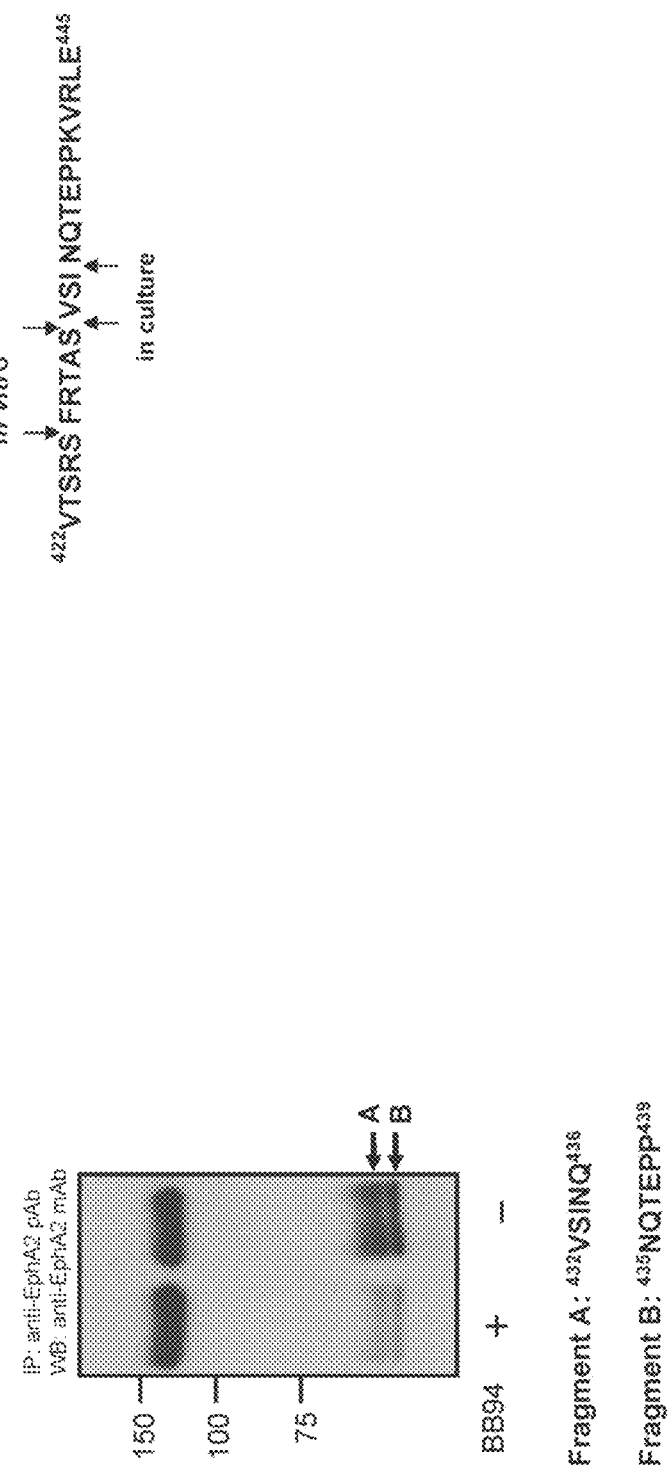

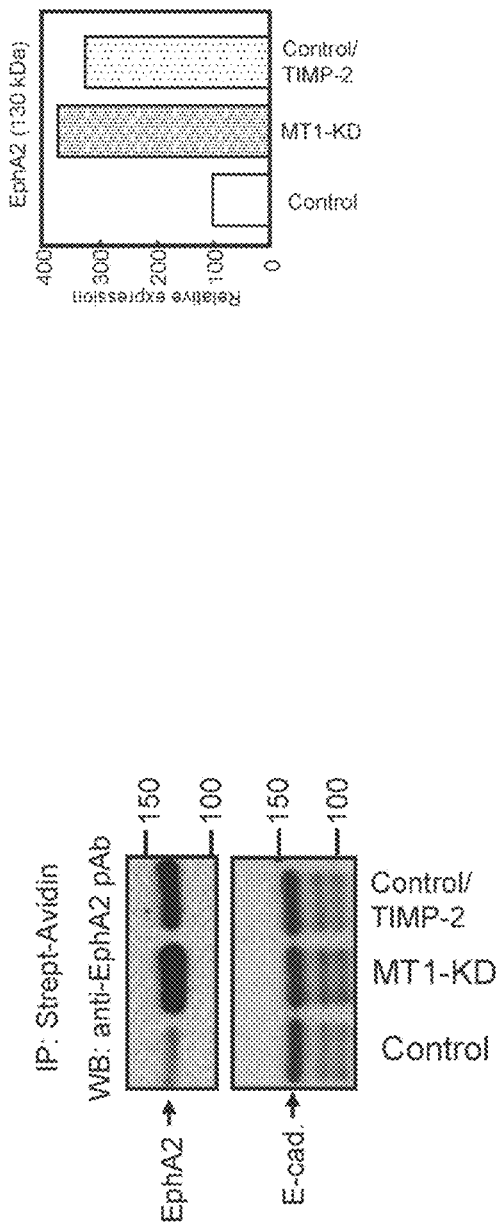

Normal ovarian tissue

Ovarian carcinoma tissue

Gastric carcinoma tissue

Colon carcinoma tissue

CANCER EXAMINATION METHOD AND EXAMINATION KIT

CROSS-REFERENCE TO RELATED APPLICATIONS

This application is a divisional of U.S. patent application Ser. No. 14/763,481, filed Dec. 15, 2015, which is a filing under 35 U.S.C. § 371 of International Patent Application No. PCT/JP2014/053355, filed Feb. 13, 2014, which claims priority to Japanese Patent Application No. 2013-206511, filed Oct. 1, 2013, and Japanese Patent Application No. 2013-026026, filed Feb. 13, 2013. Each of the foregoing applications is incorporated herein by reference in its entirety.

TECHNICAL FIELD

The present invention relates to a cancer testing method comprising detecting an EphA2 protein fragment resulting from processing by MT1-MMP.

BACKGROUND ART

Malignant tumor is one of the diseases ranking high in a death rate particularly in advanced countries and onset of it gives a strong shock to patients and their family. Identification of a signal pathway and important proteins that promote growth and metastasis of tumor cells is a promising approach for the development of a molecular targeted therapy.

Signaling proteins related to receptor tyrosine kinase (RTK) genes are often mutated in cancer cells. Even when such a mutation is not found, abnormal activation of their products can be often observed. An RTK-mediated signaling pathway is therefore a supply source rich in strong candidates for therapeutic targets.

Epinephrine-producing hepatocellular receptor A2 (EphA2) is a receptor tyrosine kinase that is widely expressed in normal epithelial cells. Eph receptor kinase has, as a member of its subfamily, 10 kinds of EphAs and 6 kinds of EphBs. EphA2 is one of EphAs.

Ligands of Eph receptors are classified into two subgroups, that is, ephrin-A and ephrin-B. Five members of ephrin-A have, at the C terminal thereof, glycosylphosphatidylinositol (GPI) and are immobilized onto a cell membrane, while members of ephrin-B are soluble. Therefore, EphA and ephrin-A bind to each other by contact between cells expressing them respectively and interaction between EphA and ephrin-A induces signaling in respective cells. Among five members of ephrin-A, A1, A3, A4, and A5 bind to EphA2. In the ephrin family, ephrin-A1 has been studied as a typical ligand of EphA2 present in a wide variety of tissues.

When ephrin-A1 binds to EphA2, autophosphorylation of a tyrosine residue at the cytoplasmic tail of EphA2 is induced. A downstream signal caused thereby inhibits signaling mediated by a growth factor receptor such as ErbB receptor. ErbB receptor stimulation activates H-ras/Erk1/2 and PI3-k/Akt and promotes cell growth, but autophosphorylation of EphA2 recruits p120Ras-GAP that down-regulates the Ras activation and suppresses growth promoting signaling. This means that EphA2 plays an important role in maintenance of epithelial cell phenotype and suppression of growth promoting signaling.

It has been reported, on the other hand, that EphA2 is highly expressed in various malignant cancers such as breast cancer, liver cancer, prostatic cancer, glioma, melanoma, ovarian adenocarcinoma, and esophageal cancer. Due to its association with a high malignancy grade and poor prognosis, it has been presumed to be promising as a molecular target of anticancer agents.

EphA2 behaves like a cancer gene product that promotes development of tumors in tumor cells. Forced expression of EphA2 in cultured cells and mice promotes growth, migration property, angiogenesis, infiltration, and metastasis of cancer cells. For example, when only EphA2 was expressed in human breast epithelial cell line MCF-10A, tumors were developed in mice. A high expression level of EphA2 induced trastuzumab resistance in HER2-positive breast cancer patients. These findings have supported the carcinogenesis promoting function of EphA2.

It has recently been reported that carcinogenesis promoting signaling by EphA2 is caused by ligand-independent activation. Without EphA2 ligand, Akt activity is not inhibited by EphA2 and ErbB receptor stimulation activates PI3K/Akt, resulting in phosphorylation of a cytoplasmic serine residue of EphA2. A GDP-GTP exchange factor Ephexin4 is recruited by a phosphorylated serine residue and activates while binding RhoG to GTP. Then, the resulting GTP-binding RhoG recruits ELMO2, Dock4, and Rac1. Thus, ligand-independent activation of EphA2 and ErbB receptor stimulation, in cooperation, causes actin reconstitution necessary for migration property or infiltration of cells. In fact, it is reported that activation of RhoG by EphA2 induces formation of protrusions of the membrane, which are called invadopodia, to promote infiltration of breast cancer cells. In addition, it is suggested that ligand-independent EphA2 activation is also involved in anoikis resistance of breast cancer cells (refer to Non-patent Documents 1-5 relating to EphA2).

Thus, the mechanism of EphA2 for aggravating cancer is being elucidated and EphA2 has been regarded promising further as a molecular target of an anticancer agent.

However, since EphA2 has two contradictory functions, that is, stabilization of the epithelial tissue and aggravation of cancer, the molecular mechanism of EphA2 how dual-directional functions of it for cancer cells are switched is required to be elucidated in order to certainly apply EphA2 to cancer therapy. In fact, EphA2 ligands are often expressed also in cancer cells and it is not clear how EphA2 is activated in the tumor tissue in a ligand-independent manner.

It is known that membrane type-1 matrix metallproteinase (MT1-MMP) is also expressed highly in malignant tumors. MT1-MMP promotes infiltration and growth of cancer cells through proteolytic action against ECM protein. MT1-MMP interacts with various cell surface proteins such as integrin, CD44, transglutaminase, and kiss-1 and some of them are cleaved by MT1-MMP.

CITATION LIST

Non-Patent Documents

Non-patent Document 1: Nat Rev Cancer. 2010 March; 10 (3):165-80.

Non-patent Document 2: Semin Cell Dev Biol. 2012 February; 23 (1):109-15.

Non-patent Document 3: Expert Opin Ther Targets. 2011 January; 15 (1):31-51.
Non-patent Document 4: Cancer Metastasis Rev. 2003: 22 (2-3):129-43.
Non-patent Document 5: J Cell Sci. 2009 Sep. 1; 122:3015-24.

DISCLOSURE OF THE INVENTION

Problem to be Solved by the Invention

An object of the present invention is to elucidate the molecular mechanism of EphA2 being activated in cancer cells in a ligand-independent manner, use EphA2 as a useful target for the cancer treatment, and provide a cancer testing method and the like using the mechanism.

Means for Solving the Problem

The present inventors have proceeded with a study in order to solve the above-mentioned problem. As a result, they have found that a ligand-binding domain of EphA2 is cleaved by MT1-MMP.

In addition, it has been confirmed that in cells in which MT1-MMP has been knocked down, ligand-dependent autophosphorylation of EphA2 is enhanced; Erk1/2 and Akt activities induced by EGF are significantly suppressed by the MT1-MMP knockdown in the presence of a ligand; similar results are observed in various cancer cells expressing EphA2 but not observed in cancer cells not expressing EphA2; growth of cells in which MT1-MMP has been knocked down is suppressed in a ligand-dependent manner; and EGF-induced RhoG activity or cell migration of the cells in which MT1-MMP has been knocked down is suppressed significantly in the presence of a ligand.

It has been confirmed further that when cells expressing an EphA2 mutant having resistance against processing by MT1-MMP are transplanted to mice, metastasis to the lung is suppressed significantly compared with cells expressing wild type MT1-MMP.

Further, from the results of an experiment using a frozen carcinoma tissue section from ovarian cancer, it has been suggested that EphA2 is processed by MT1-MMP even in the carcinoma tissue in vivo and it has been confirmed that processing of EphA2 by MT1-MMP has a strong correlation with aggravation of cancer. Furthermore, when normal ovarian tissue and ovarian carcinoma tissue were immunostained with an antibody capable of recognizing the N terminal side of EphA2 and an antibody capable of recognizing the C terminal side thereof, the carcinoma tissue was not stained with the antibody capable of recognizing the N terminal side. It has therefore been confirmed that EphA2 was cleaved in the cancer tissue, but EphA2 was intact in the normal tissue. It has been confirmed further that this phenomenon has occurred similarly in gastric cancer or colon cancer.

It has been confirmed further that when an EphA2 mutant not cleaved by MT1MMP was expressed in cancer cells (A431 cells), a phenotype of the cancer cells changed to a normal epithelial cell-like one; and that a fragment obtained by expressing normal EphA2 in A431 cells and cleaving it by endogenous MT1-MMP can be detected using an antibody, leading to the completion of the present invention.

The present invention relates to:

[1] a method of testing cancer, comprising a step of measuring an amount of a fragment of EphA2 protein having a molecular weight of from 30 kDa to 80 kDa in a sample derived from a subject;

[2] the method as described above in [1], wherein the fragment of EphA2 protein is a fragment comprising the N terminal of EphA2 protein;

[3] the method as described above in [1], wherein the fragment of EphA2 protein is at least one of the following peptides (i) to (iii):
(i) a peptide having any one of the amino acid sequences set forth in SEQ ID NO: 1 to 4;
(ii) a peptide having an amino acid sequence obtained by adding, substituting, or deleting one or more amino acids from any one of the amino acid sequences set forth in SEQ ID NO: 1 to 4; and
(iii) a peptide having an amino acid sequence having 80% or more sequence identity with any one of the amino acid sequences set forth in SEQ ID NO: 1 to 4:

[4] the method as described above in any one of [1] to [3], wherein the cancer expresses EphA2;

[5] the method as described above in any one of [1] to [4], wherein the sample is at least one selected from blood, lymph, urine, and feces;

[6] the method as described above in any one of [1] to [5], which is performed to estimate an effect or side-effect of an anticancer agent;

[7] the method as described above in any one of [1] to [6], wherein the amount of a fragment of EphA2 protein is measured using an antibody capable of recognizing the EphA2 fragment;

[8] the method as described above in [7], wherein an epitope of the antibody capable of recognizing the EphA2 fragment is located in a cysteine-rich domain of EphA2 protein;

[9] a kit for testing cancer, including an antibody capable of detecting a fragment of EphA2 protein having a molecular weight of from 30 kDa to 80 kDa;

[10] the kit as described above in [7], wherein the fragment contains an N terminal of EphA2 protein;

[11] the kit as described above in [9] or [10], wherein an epitope of the antibody is in a cysteine-rich domain on EphA2 protein;

[12] the kit as described above in [9] or [10], wherein the antibody is an antibody against at least one of the following peptides (i) to (iii):
(i) a peptide having any one of the amino acid sequences set forth in SEQ ID NO: 1 to 4;
(ii) a peptide having an amino acid sequence obtained by adding, substituting, or deleting one or more amino acids from any one of the amino acid sequences set forth in SEQ ID NO: 1 to 4; and
(iii) a peptide having an amino acid sequence having 80% or more sequence identity with any one of the amino acid sequences set forth in SEQ ID NO: 1 to 4;

[13] a kit for testing as described above in [9] or [12], wherein the kit is used for estimating an effect or side-effect of an anticancer agent;

[14] a method of screening an anticancer agent, including:
culturing a cell expressing EphA2 under conditions where MT1-MMP processes EphA2,
adding a test compound to a culture medium of the cell and incubating in the presence of MT1-MMP, and
determining whether EphA2 is processed or not.

[15] the screening method as described above in [14], wherein in the step of determining whether EphA2 is processed or not, the test compound which lowers processing compared with processing in the absence of the test compound is selected as a candidate for the anticancer agent; and

[16] an anticancer agent containing a double stranded RNA having any of the following sequences:

```
siRNA #1
                                    (SEQ ID NO: 6)
S: ggauggacacggagaauuutt (SEQ ID NO: 7)
AS: aaauucuccguguccaucctt siRNA #2
                                    (SEQ ID NO: 8)
S: gcgaugaagucuucacuuatt, (SEQ ID NO: 9)
AS: uaagugaagacuucaucgctt,
and siRNA #3
                                    (SEQ ID NO: 10)
S: ggguagagacccugagacatt (SEQ ID NO: 11)
AS: ugucucagggucucuaccctt,
``` or a precursor thereof, or a nucleic acid encoding the RNA or precursor; and

[17] a method of treating cancer including inhibiting expression or function of MT1-MMP.

Effect of the Invention

According to the cancer testing method and testing kit of the present invention, onset, aggravation, prognosis, and the like of cancer can be determined by a simple method of detecting an EphA2 fragment cleaved by MT1-MMP.

According to the screening method of the present invention, a molecular target drug candidate capable of suppressing only a ligand-independent activity of EphA2 can be selected.

BRIEF DESCRIPTION OF THE DRAWINGS

FIG. 1C shows the results of analyzing the N-terminal amino acid of Fragments A and B (on the stud side) processed by MT1-MMP. After the EphA2 having Myc-labeled C-terminal and a wild type MT1-MMP were co-expressed in HT1080 cells and full-length type EphA2 and Fragments A and B were purified from the resulting cells by immunoprecipitation with a Myc antibody, the purified EphA2 and Fragments A and B were detected by western blotting with a Myc antibody. From the cells treated with BB94, only a full length type EphA2 was purified. Analysis of the N terminal of Fragments A and B by a peptide sequencer has revealed that Fragment A was VSINQ and Fragment B was NQTEPP. The result has suggested the possibility of different processing occurring at two sites on the cell membrane. FIG. 1D shows the results of synthesizing a peptide chain including a cleavage site found in FIG. 10 and carrying out in vitro digestion of the peptide chain with a recombinant protein of MT1-MMP, in order to identify the cleavage site of EphA2 by MT1-MMP. In in vitro digestion, MT1-MMP cleaved two sites (arrows) between S426 and F427 and between S431 and V432, each of the EphA2 peptide. The results of FIGS. 1C and 1D have suggested that MT1-MMP cleaved between S431 and V432 on the cell membrane and in conjunction with this cleavage, an unknown protease cleaved between I434 and N435.

FIG. 2 (A-G) shows the results of studying, by IP-western, EphA2 processing and a phosphorylation state of EphA2 by Ephrin-A1 while using A431 cells whose MT1-MMP expression has been knocked down by siRNA. FIG. 2E shows the results of biotinylating the surface layer of A431 cells in order to detect processing of EphA2 in the surface layer of cells, purifying a membrane protein fraction by pulldown with avidin beads, and measuring an amount of EphA2 in the purified membrane protein by western blotting with an EphA2 antibody. FIGS. 2F and 2G show the results of relative expression of EphA2 and E-cadherin based on the results of FIG. 2E. MT1-MMP knockdown increased the full-length EphA2 amount and also TIMP-2 treatment produced the same results (FIGS. 2E, 2F). Presence or absence of expression of MT1-MMP did not have any influence on the expression amount of E-cadherin in the cell surface layer (FIGS. 2E, 2G).

FIG. 3A shows the results of detecting EphA2 and p-EphA2 by IP-western with an antibody capable of recognizing the C terminal of EphA2 and detecting p-Erk1/2, Erk1/2, p-Akt, and Akt by western blotting with antibodies specific thereto, respectively. Phosphorylation levels of them were quantified by densitometry using Image J. In the presence of Ephrin-A1, presence or absence of expression of MT1-MMP had no influence on the activation of an EGF receptor (FIGS. 3A, 3B). The MT1-

Figure 3A:
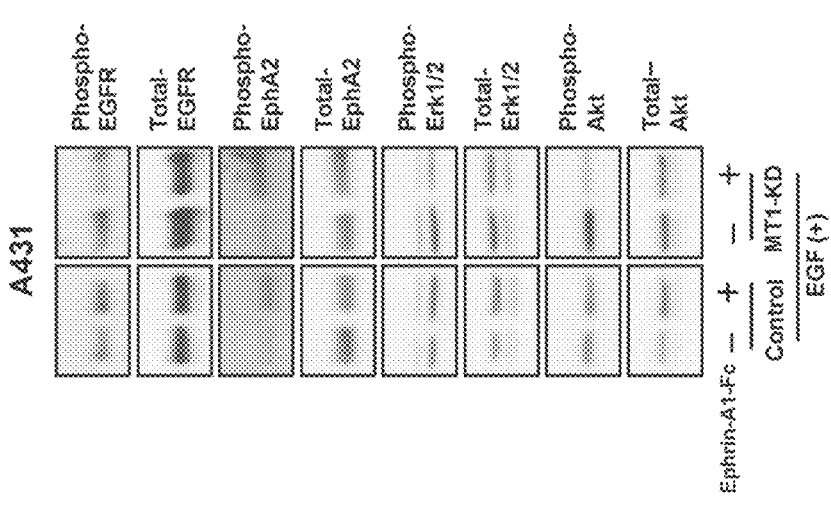
FIGS. 3A to 3F show the results of treating, with EGF, A431 cells whose MT1-MMP expression was knocked down by siRNA and studying the influence of EphA2 on EGF receptor downstream signaling (PI3K, MAPK) in an Ephrin-A1 dependent manner.
Figure 3B:
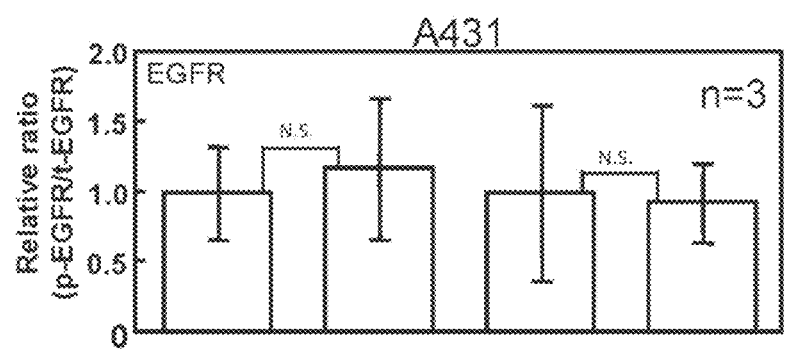
Figure 3C:
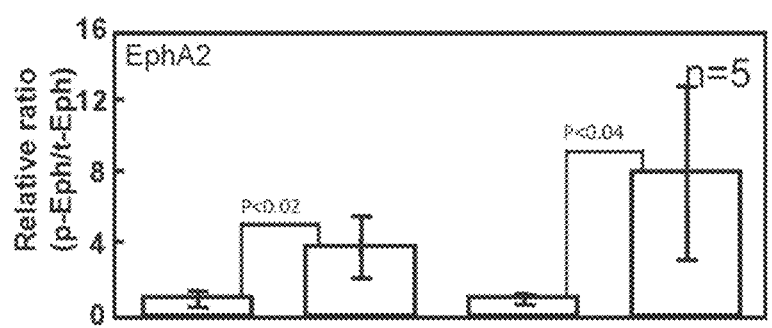
Figure 3D:
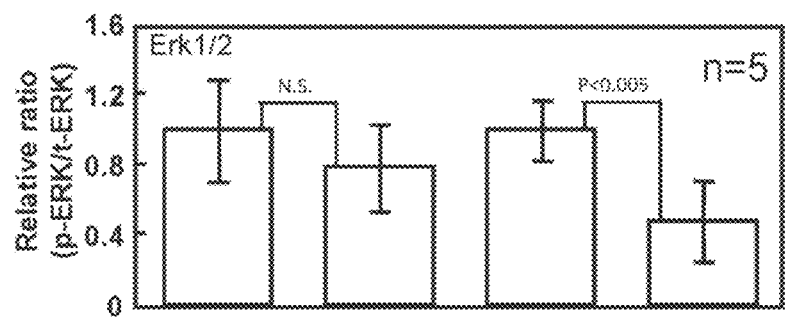
Figure 3E:
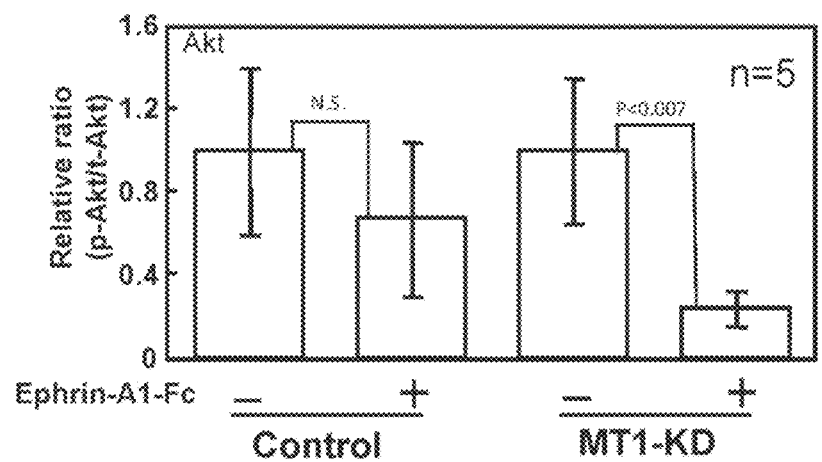
Figure 3F:
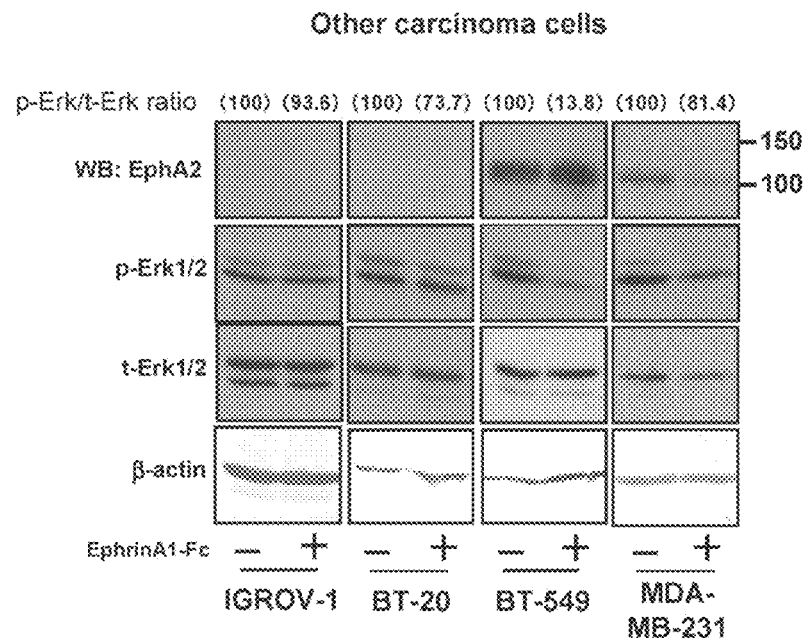

MMP knockdown enhanced the phosphorylation of EphA2 itself (FIGS. 3A, 3C). Erk1/2 and Akt activities induced by EGF in the presence of Ephrin-A1 were suppressed significantly by the MT1-MMP knockdown (FIGS. 3A, 3D, and 3E). Similar results were observed in human breast cancer BT549 cells and head and neck cancer SCC61 cells (FIG. 3F, FIG. 8). Such results were observed in none of ovarian carcinoma IGROV-1 cells and breast cancer BT-20 cells that did not express EphA2, and MDA-MB-231 cells having k-ras mutation (FIG. 3F).

Figure 3G:
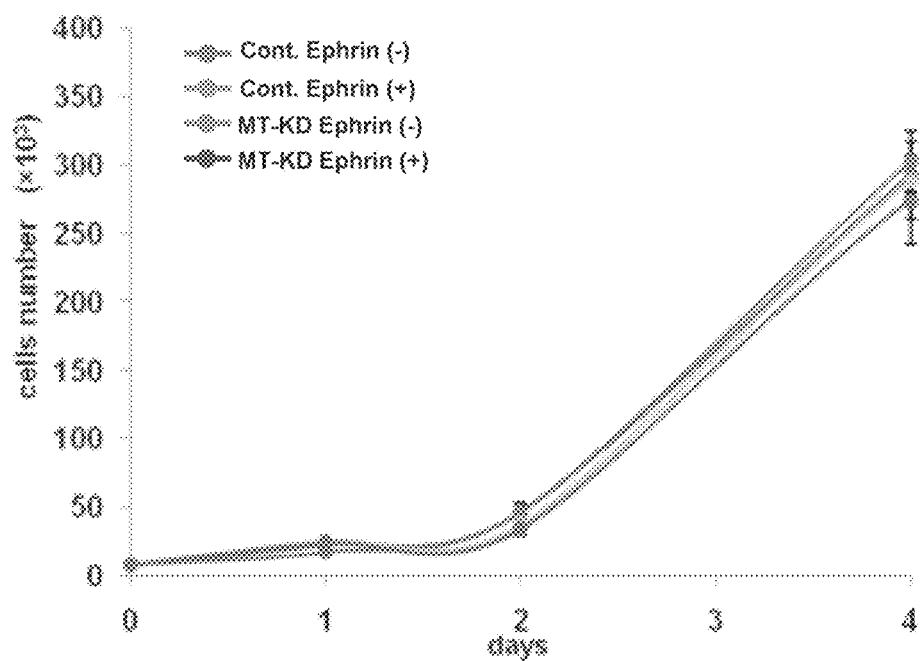
Figure 3H:
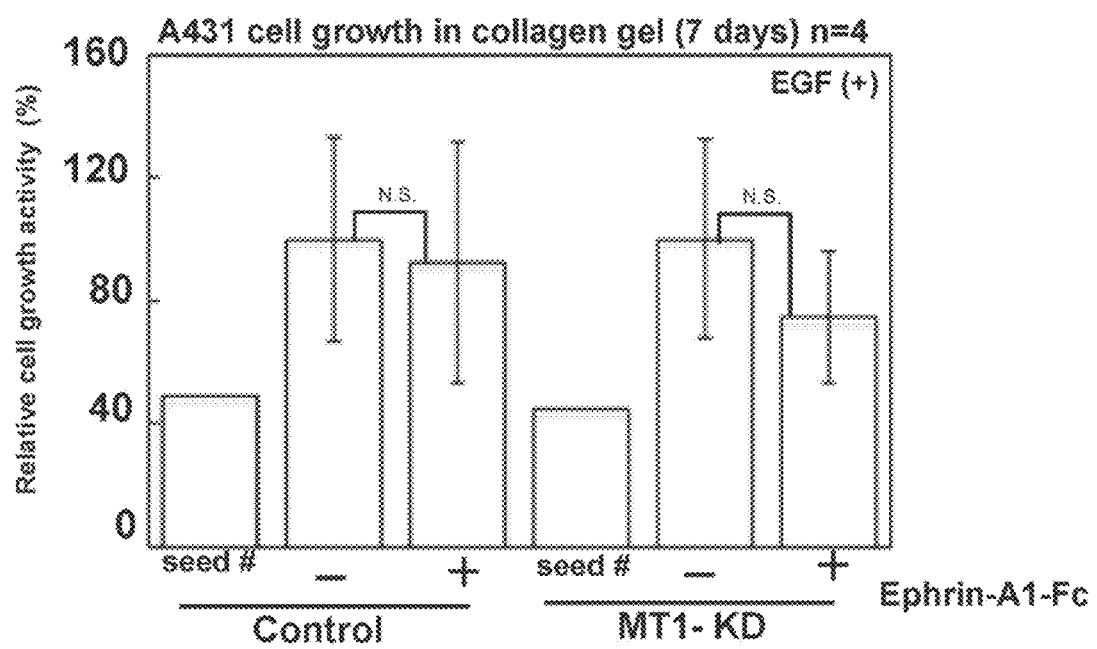
Figure 3I:
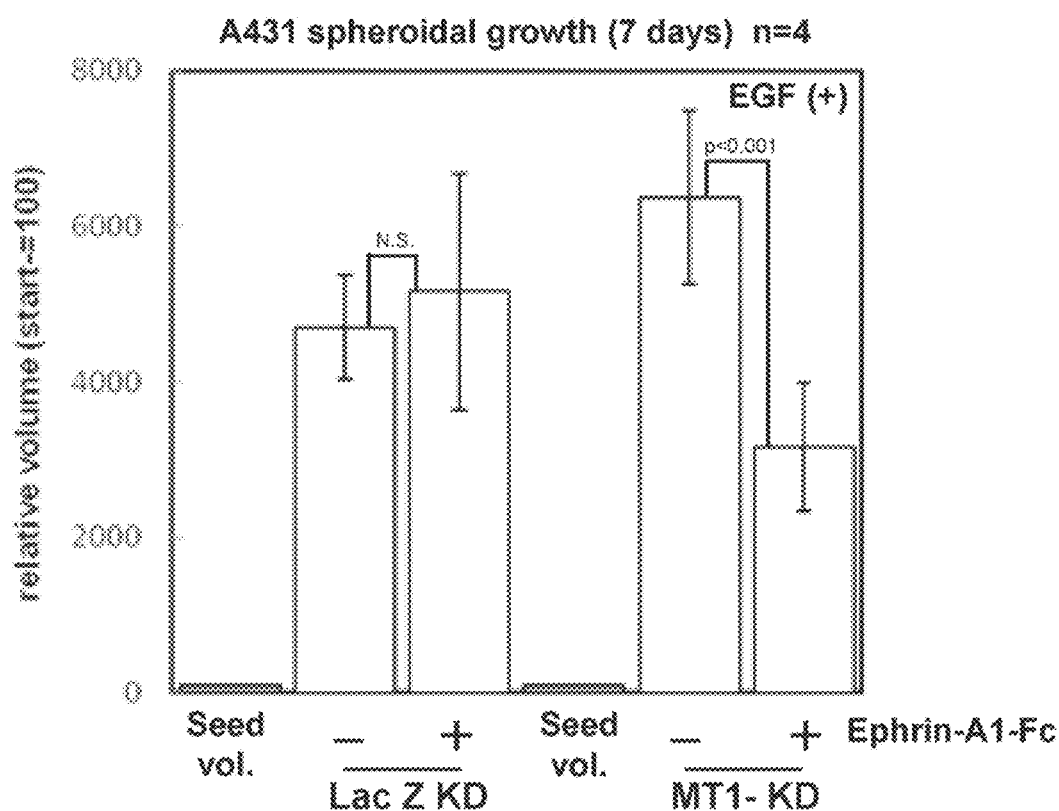
Figure 4A:
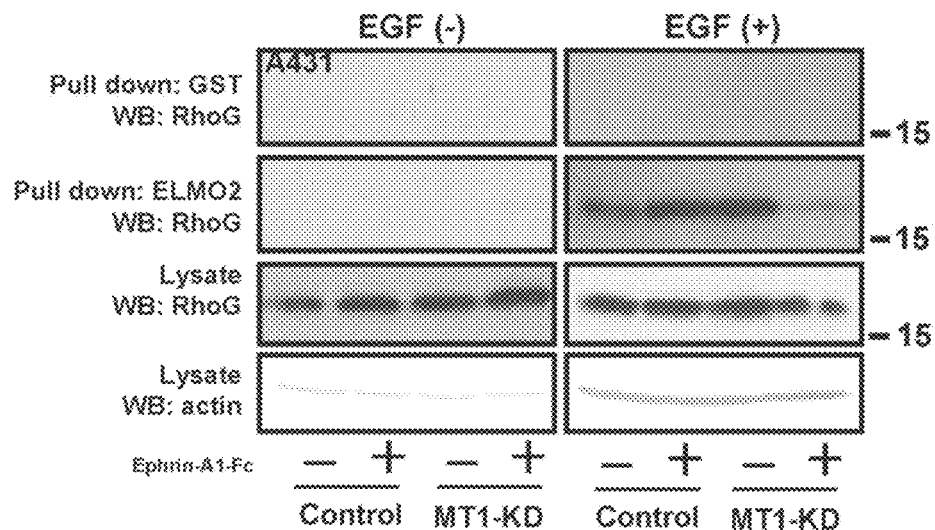
Figure 4B:
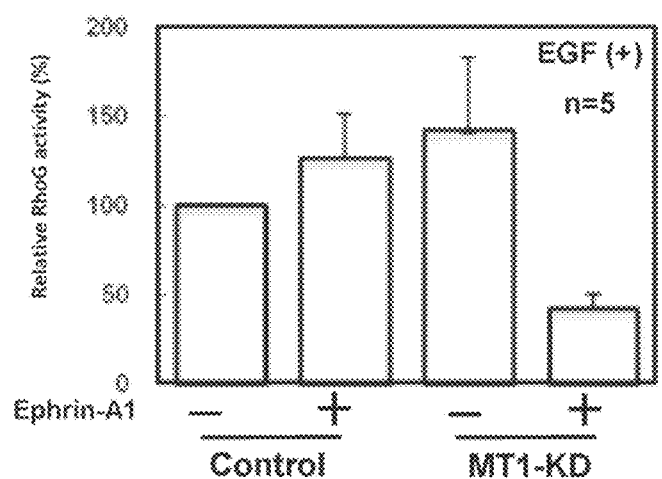
Figure 4C:
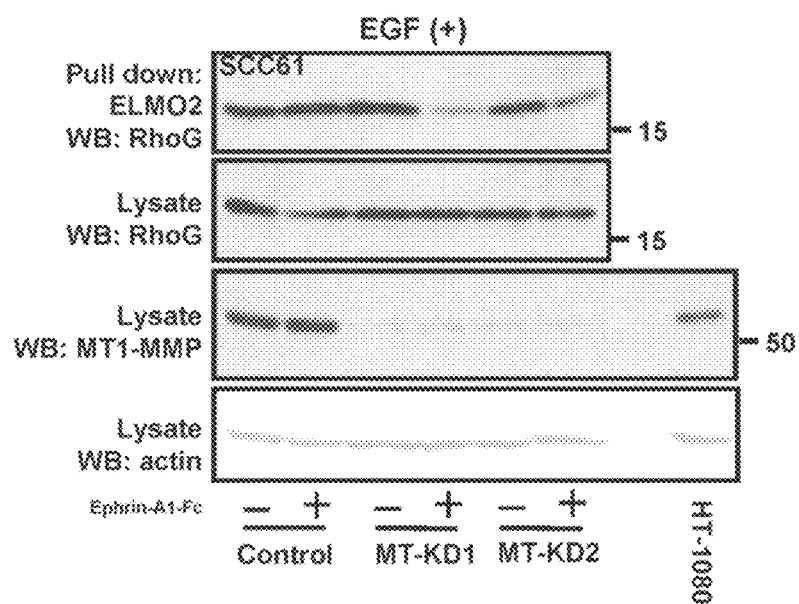
Figure 4D:
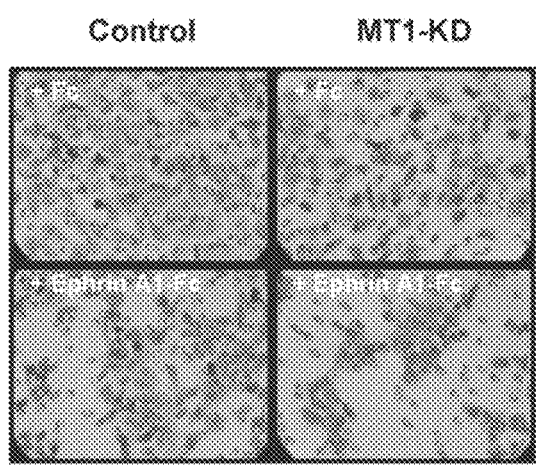
Figure 4E:
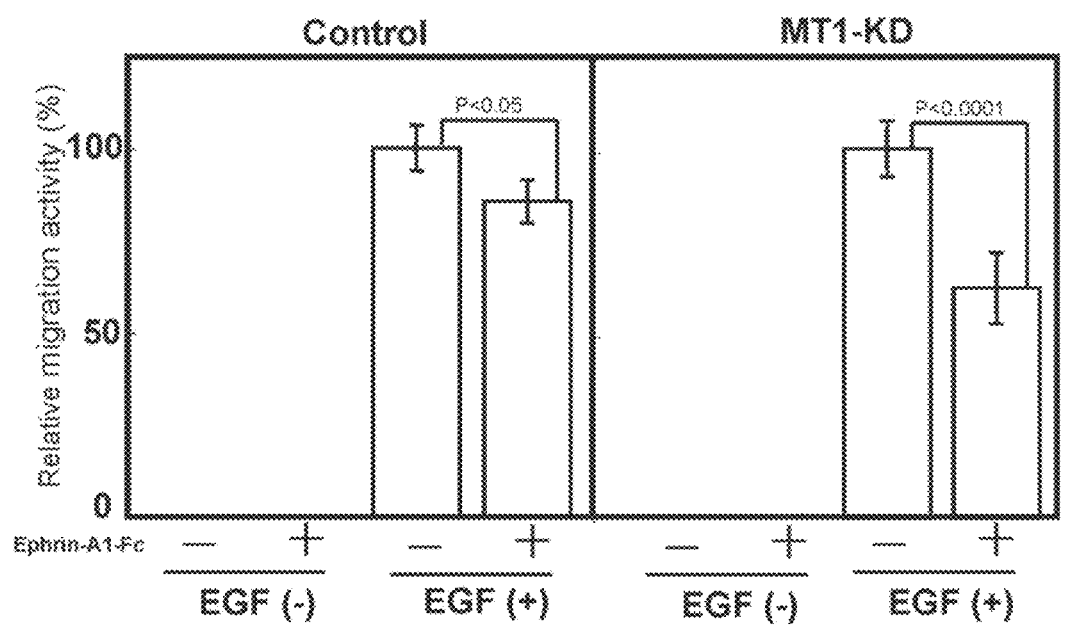

FIGS. 3G to 3I show the results of studying the influence of EphA2 processing on EphA2/Ephrin-A1 dependent cell growth inhibition by two-dimensional and three-dimensional (in collagen gel) and anchorage-independent culture. The two-dimensional or three-dimensional cell growth activity was determined by counting the number of viable cells using a hemacytometer (FIGS. 3G, 3H), while spheroidal growth activity was determined by comparing the measured volumes of the spheroids (FIG. 3I). Under the conditions in the two-dimensional culture dish, no influence of the presence or absence of MT1-MMP on the Ephrin-A1/EphA2 dependent cell growth inhibition was observed (FIGS. 3G, 3H). In the three-dimensional culture in the collagen gel and anchorage-independent spheroid formation, however, growth of MT1-MMP knockdown cells was significantly suppressed in an Ephrin-A1 dependent manner (FIG. 3I). Experiments were performed independently four times and T-test was used for statistical processing.

FIG. 4 (A-E) shows the results of studying the influence of Ephrin-A1-dependent EphA2 on signaling of small GTPase RhoG downstream of the EGF receptor while using A431 cells whose MT1-MMP expression was knocked down by siRNA. The RhoG activity was detected using, as a bait, ELMO2/GST fusion protein serving as an effector of RhoG bound to glutathione beads. RhoG activity was quantified by densitometry with Image J. The RhoG activity was not detected in the cells not treated with EGF (FIG. 4A). On the other hand, after stimulation with EGF, the MT1-MMP knockdown cells had significantly reduced RhoG activity by the treatment with Ephrin-A1 (FIGS. 4A, 4B). Similar results were found in SCC61 cells (FIG. 4C). Study of the migration activity of the EGF-stimulated cells in a transwell chamber has revealed that the cell migration was significantly suppressed in the MT1-MMP knockdown cells by the Ephrin-A1 treatment (FIGS. 4D, 4E). This has suggested that processing of EphA2 by MT1-MMP had a role of enhancing a small GTPase activity. The experiment was performed five times and three times independently and a T-test was used for statistical processing.

FIG. 5 (A-G) shows the results of an experiment made using cells expressing a processing-resistant EphA2 mutant in order to study the possibility that EphA2 processing by MT1-MMP enhances metastasis activity of cancer cells. A431 cells having only a vector, wild type EphA2, and a processing-resistance EphA2 mutant introduced therein were established, respectively (FIGS. 5A, 5B). In the drawing, SP represents a signal peptide, EBD represents Ephrin-binding domain, TM represents transmembrane, and F represents FLAG. As a result of detection, by western blotting, of the processed state of EphA2 of the cells having wild type EphA2 or a processing-resistant EphA2 mutant introduced therein, a cleavage site-deficient mutant showed resistance against processing by MT1-MMP (FIG. 5C). Phosphorylation of the EphA2 mutant with Ephrin-A1 was confirmed by immunoprecipitation using an EphA2 antibody (FIG. 5D).

In order to study the influence of the EphA2 mutant to the metastasis activity of A431 cells to the lung, an experimental mouse lung metastasis embodiment was prepared and the influence was verified (n=5). Each cell ($5 \times 10^6/100$ μl) was administered to the tail vein of the mouse. One month later, the mouse was dissected and metastatic nodules formed in the lung were observed. In the mouse administered with cells having processing-resistant EphA2 mutation introduced therein showed reduction in formation of metastatic nodules in the lung (FIGS. 5E, 5F). Results of HE staining showed that growth of cancer cells in the lung was also suppressed significantly in the mouse administered with the cells having processing-resistant EphA2 mutation introduced therein (FIG. 5G). T-test was used for statistical processing.

FIG. 6 (A-F) shows the results of studying the processing of EphA2 in ovarian carcinoma. FIG. 6A shows the results of measuring, by CBB, a tissue protein mass of each of tissue extract solutions prepared from a frozen carcinoma tissue section by using a RIPA buffer and then, analyzing EphA2 and MT1-MMP that have expressed in each tissue by western blotting with each of an antibody against the C terminal of EphA2 and a MT1-MMP monoclonal antibody. As a positive control, the EphA2 fragment and MT1-MMP contained in the lysate extracted from A431 cells having MT1-MMP (±MMI) introduced therein were used. In the ovarian carcinoma tissue, only a low level of the full-length type EphA2 (intact) was detected and the fragment (EphA2 fragment) having a molecular weight of 60 kDa was main (FIG. 6A, lower panel). An expression amount of MT1-MMP in these tissues was detected using an MT1-MMP monoclonal antibody (FIG. 6A, upper panel). The band with "*" was observed without a primary antibody so that it was presumed to be a non-specific band (FIG. 6B). These results have suggested that even in the in vivo carcinoma tissue, EphA2 was processed by MT1-MMP and produced a 60-kDa fragment attributable to processing.

Figure 6A:
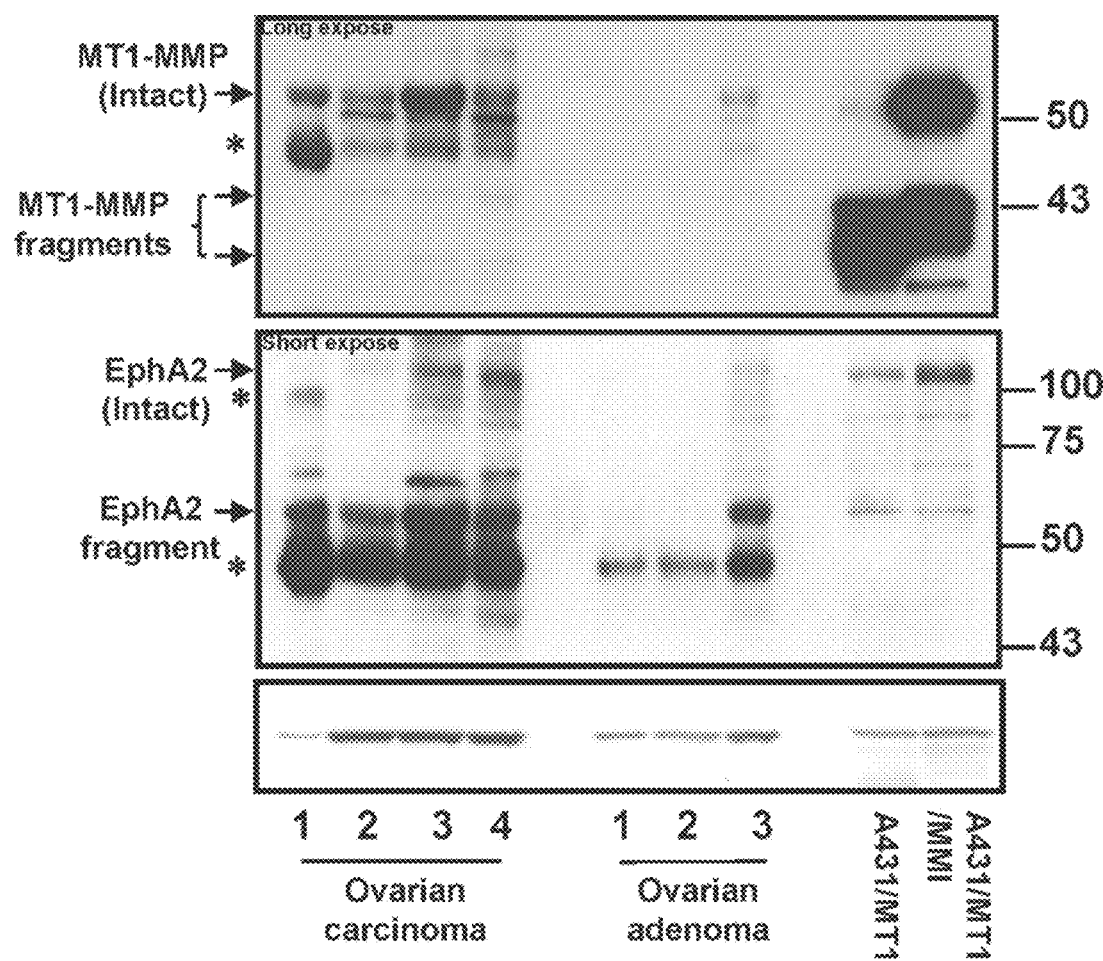
Figure 6B:
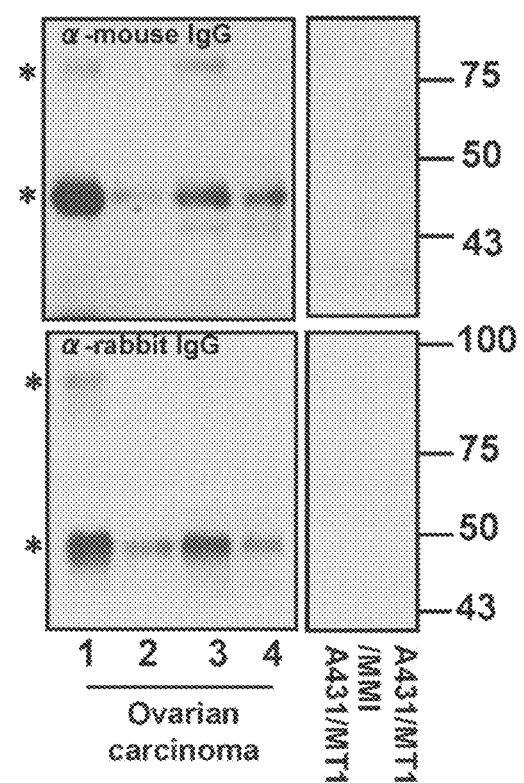
Figure 6C:
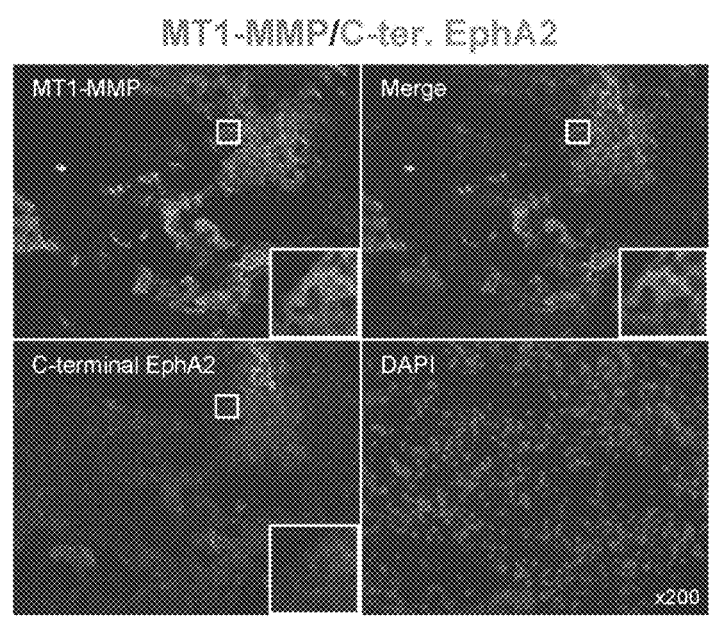
Figure 6D:
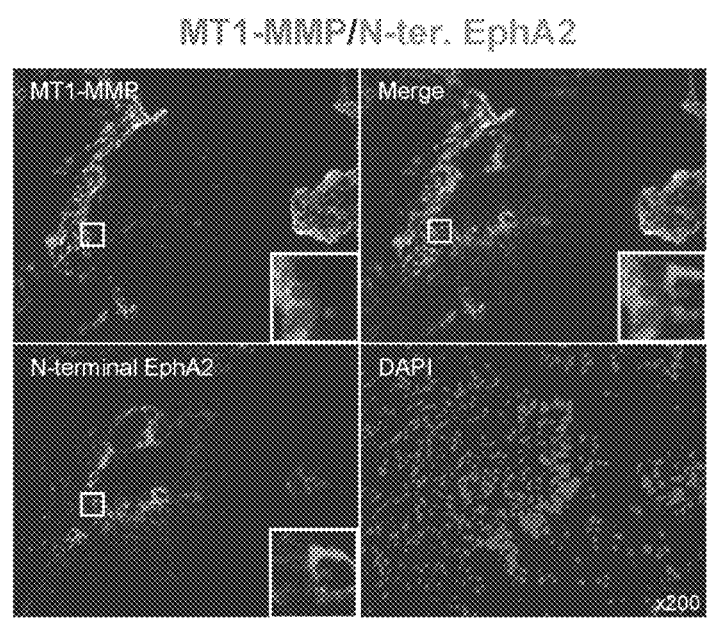

FIGS. 6C and 6D show the results of detecting EphA2 and MT1-MMP of the ovarian carcinoma tissue by immunostaining under a fluorescence microscope. EphA2 was co-stained with a MT1-MMP antibody by using antibodies capable of recognizing the C terminal (FIG. 6C) and N terminal (FIG. 6D), respectively. The positive stained site of MT1-MMP and a positive site of the C-terminal antibody of EphA2 (FIG. 6C) show co-localization. On the other hand, a positive stained site of the N-terminal antibody of EphA2 and that of MT1-MMP do not show co-localization (FIG. 6D). This has suggested the possibility that many EphA2s that have highly expressed in the carcinoma tissue are each a stud cleaved at the N terminal thereof.

Figure 6E:
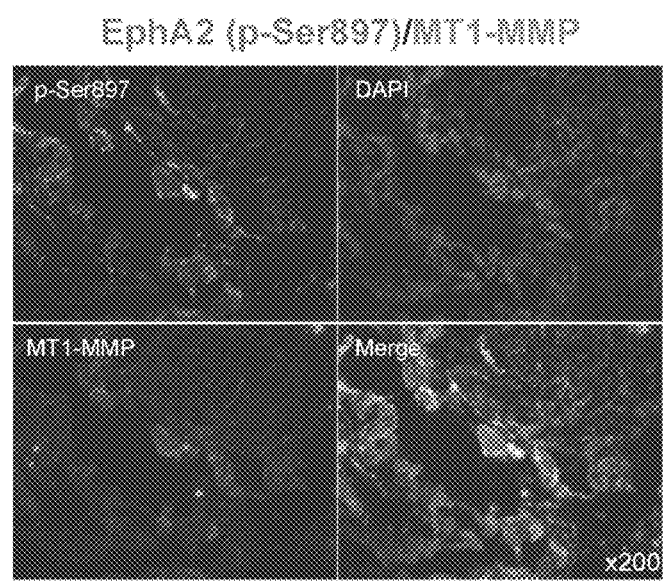
Figure 6F:
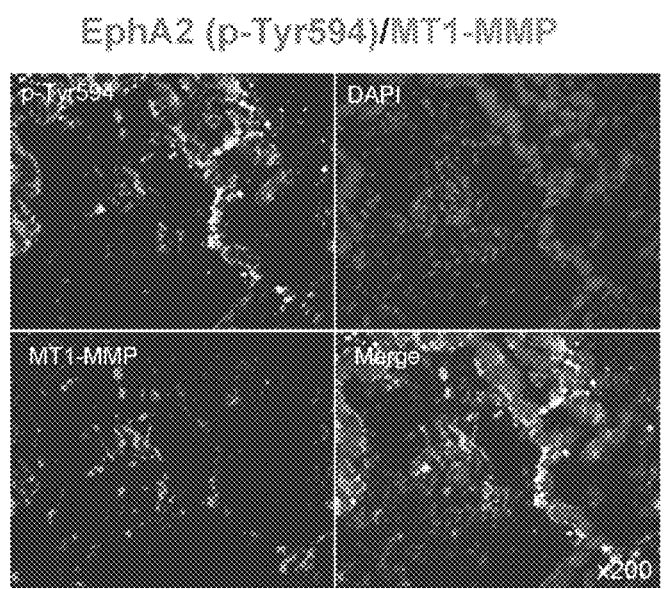

FIGS. 6E and 6F show the results of studying the phosphorylation kinetics of EphA2 at the expression site of MT1-MMP by using two antibodies capable of recognizing phosphorylation of the intracellular domain of EphA2. In the ovarian carcinoma tissue, expression of MT1-MMP and expression of ligand-independent serine 897 residue phosphorylation of EphA2 (FIG. 6E) showed co-localization. On the other hand, expression of MT1-MMP and expression of ligand-dependent tyrosine 594 residue phosphorylation showed different localization (FIG. 6F).

Figure 7A:
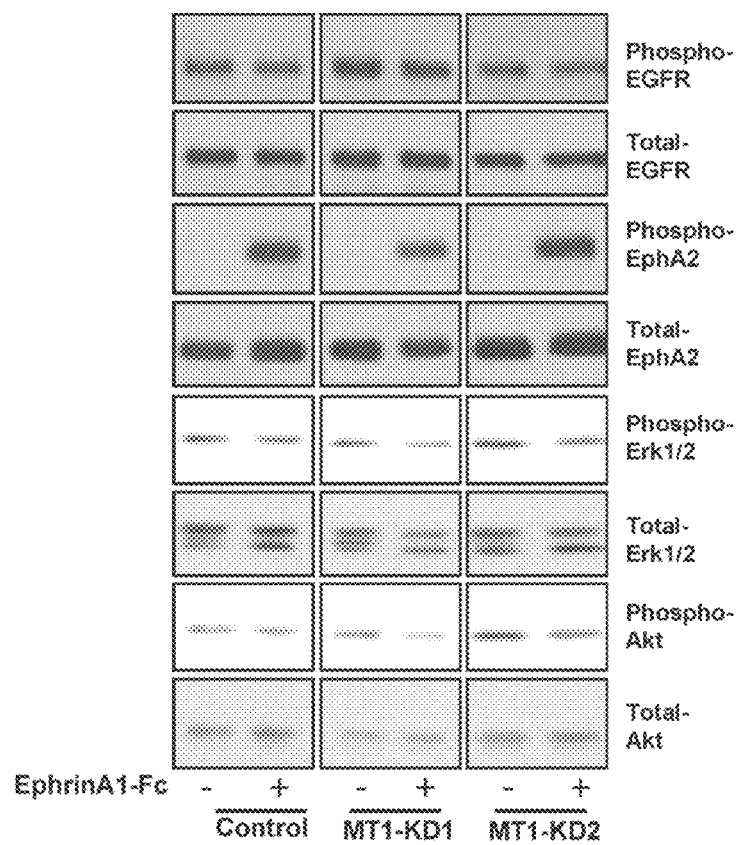
Figure 7B:
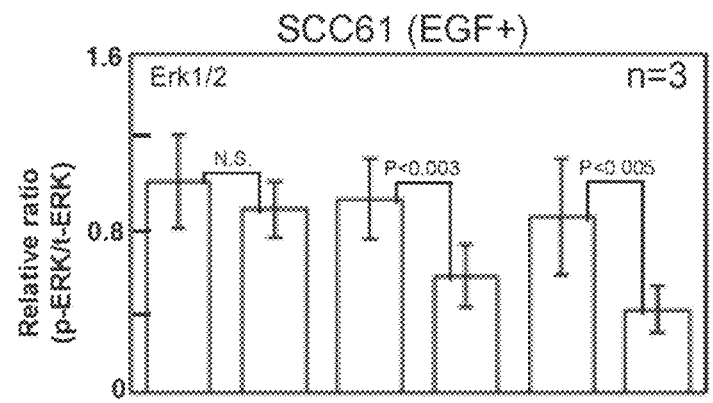
Figure 7C:
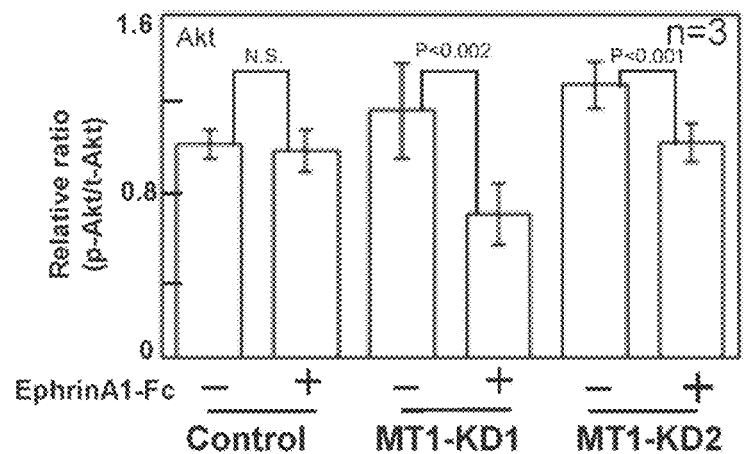
Figure 8A:
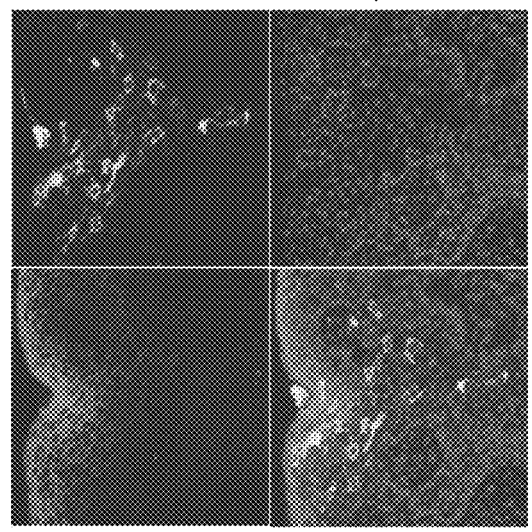
Figure 8B:
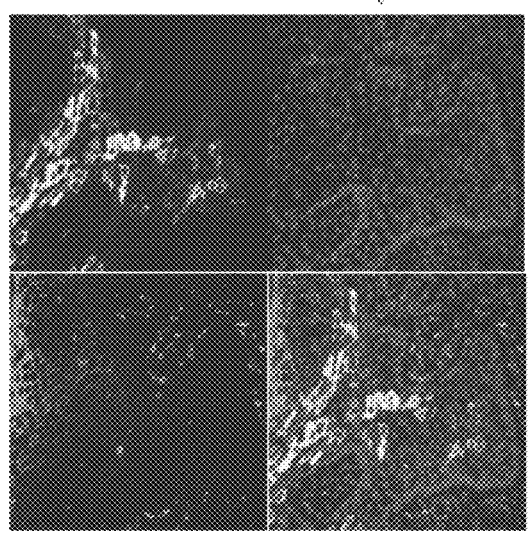
Figure 8C:
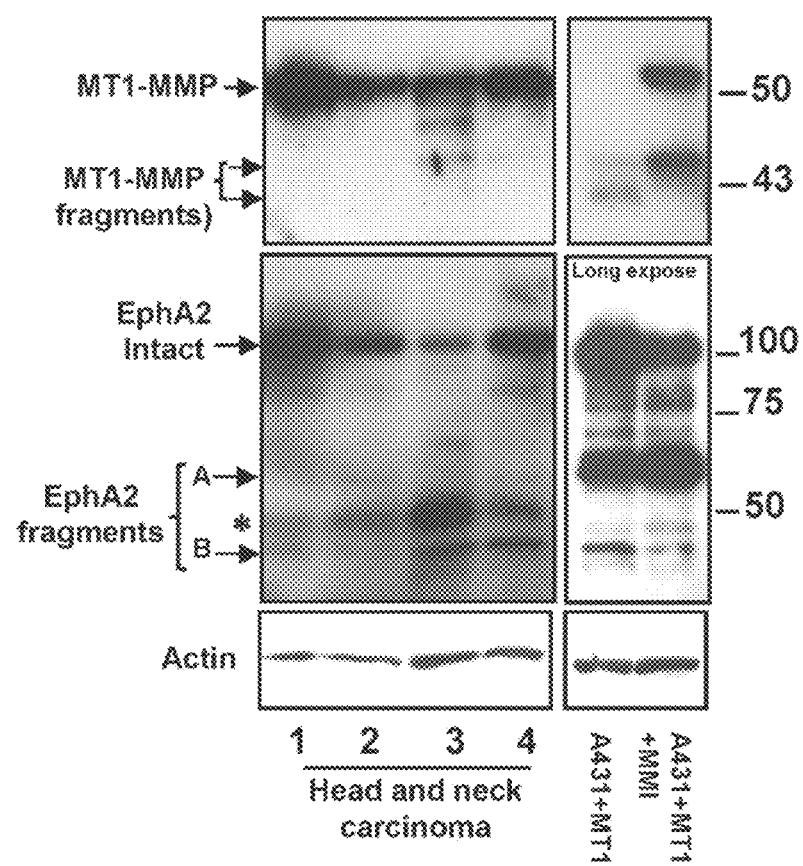

FIG. 7 (A-C) shows the results of studying the influence of MT1-MMP knockdown on EphA2/Ephrin-A1 signaling by using the human head and neck cancer cells SCC61. Phosphorylation of EGFR, EphA2, Erk1/2, and Akt of EGF-stimulated SCC61 cells was studied using IP and WB. A phosphorylation ratio of Erk1/2 and Akt was quantified by densitometry with Image J. Experiments were performed three times independently and a T-test was used for statistical processing FIG. 8 (A-C) shows the results of analyzing the head and neck carcinoma tissue in a manner similar to that of FIG. 6. Since the MT1-MMP expression was lower than that in the ovarian carcinoma, an EphA2 processing rate was very low (FIG. 8C, lower panel). The head and neck carcinoma tissue was analyzed by immunostaining. As a result, EphA2 was expressed in a tumor portion and a non-tumor portion, while MT1-MMP showed a partial expression distribution in a tumor portion (FIGS. 8A, 8B). These results have suggested that also in the head and neck carcinoma, processing of EphA2 similar to that in the ovarian carcinoma tissue occurred in tumor cells expressing MT1-MMP.

Figure 9A:
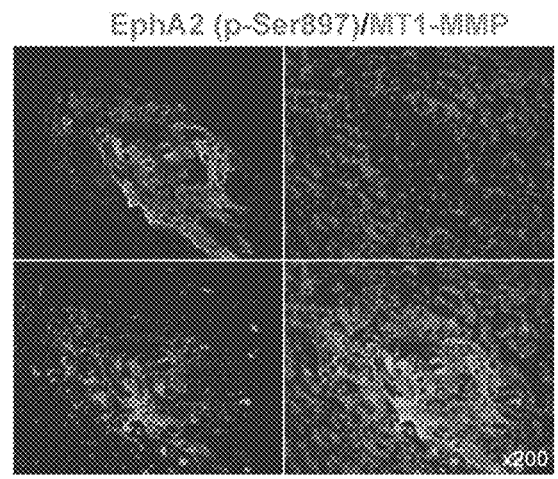
Figure 9B:
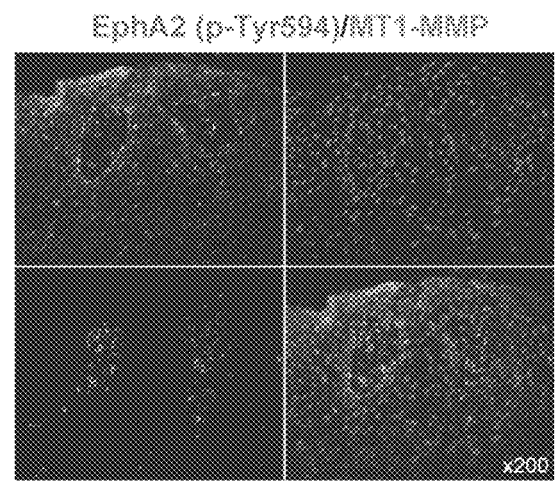

FIG. 9 (A, B) shows the results of an experiment made on the head and neck carcinoma tissue. It shows the results of studying the phosphorylation kinetics of EphA2 at the MT1-MMP expression site by using two antibodies capable of recognizing phosphorylation of the intracellular domain of EphA2. Also in the head and neck carcinoma tissue, expression of MTI-MMP and expression of ligand-independent phosphorylation of serine 897 residue of EphA2 (FIG. 9A) showed co-localization. On the other hand, expression of MT1-MMP and expression of ligand-dependent phosphorylation of tyrosine 594 residue showed different localization (FIG. 9B).

Figure 10:
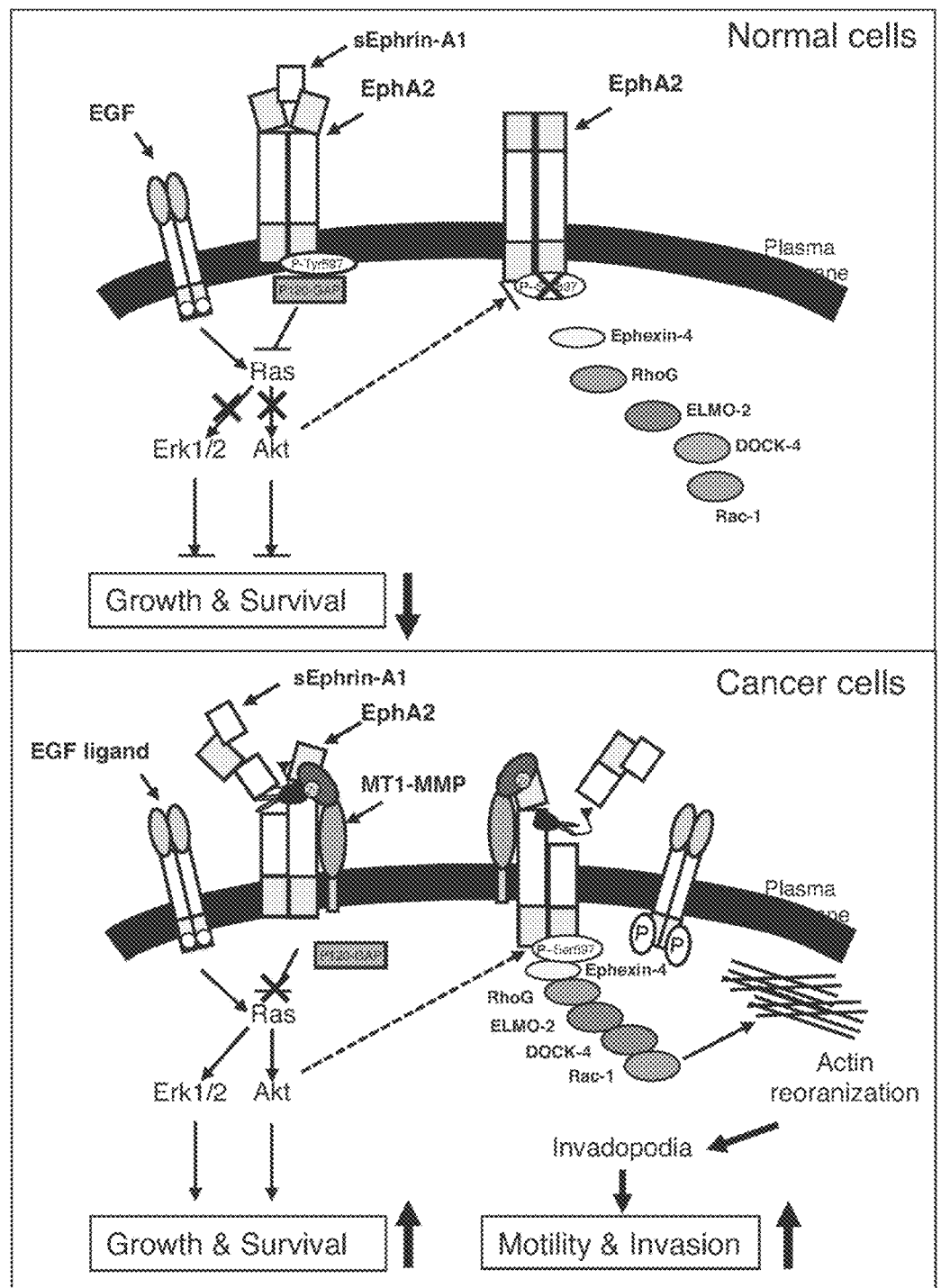

FIG. 10 is a schematic view of a embodiment in which MT1-MMP converts EphA2 to ligand-insensitive. In normal cells, EphA2 functions in a ligand-dependent manner and controls to suppress signaling for cell growth or survival. On the other hand, when MT1-MMP expression is enhanced with the progression of canceration of cells and a ligand-binding domain is released from EphA2, this EphA2 is converted into a ligand-insensitive RTK. EphA2 therefore acts in a ligand-independent manner and each signaling pathway is activated to control cells to promote growth, survival, and migration. This contributes to acquisition of a malignant phenotype of cancer cells.

Figure 11A:
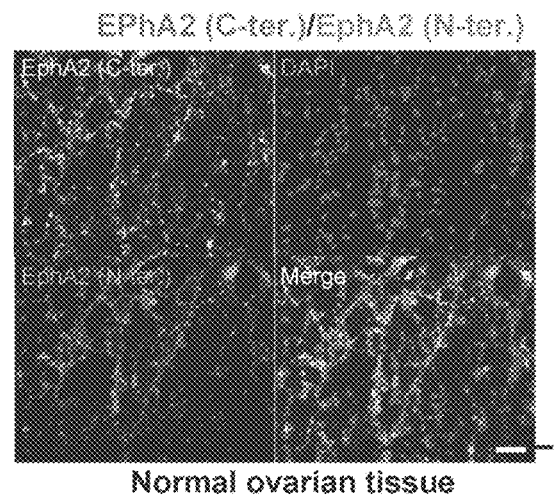
Figure 11B:
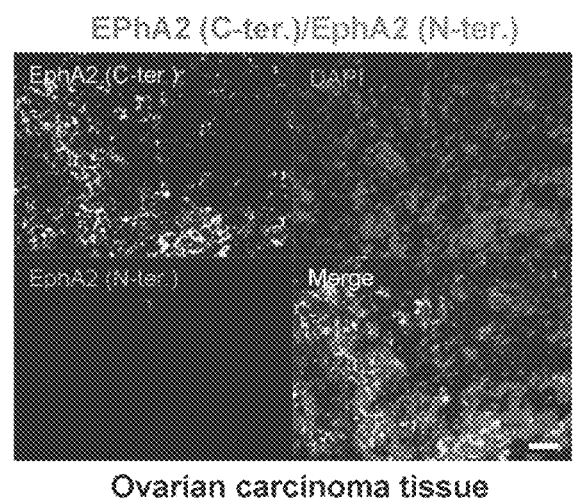

FIG. 11 (A, B) shows results of immunostaining the normal ovarian tissue (FIG. 11A) and the ovarian carcinoma tissue (FIG. 11B) with an antibody capable of recognizing the N terminal side of EphA2 and an antibody capable of recognizing the C terminal side. Nuclei were stained with DAPI. The bar corresponds to 50 µm. In immunostaining with the antibody capable of recognizing the C terminal side of EphA2, results were similar between the normal ovarian tissue and the ovarian carcinoma tissue, while the ovarian carcinoma tissue was not stained with the antibody capable of recognizing the N terminal side.

Figure 12A:
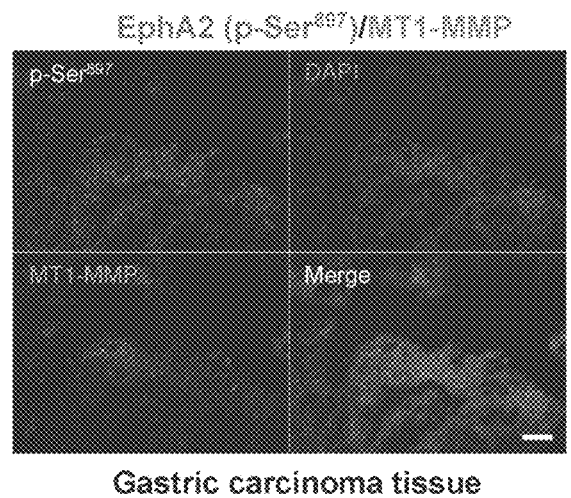
Figure 12B:
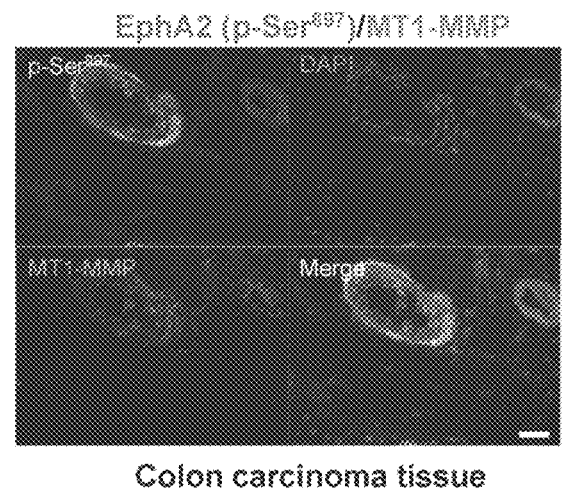

FIG. 12 (A, B) shows the results of immunostaining the gastric carcinoma tissue (FIG. 12A) and the colon carcinoma tissue (FIG. 12B) with an antibody which detects ligand-independent serine 897 phosphorylation of EphA2 and an antibody capable of detecting MT1-MMP. Nuclei were stained with DAPI. The bar corresponds to 50 µm. Also in the gastric carcinoma tissue and the colon carcinoma tissue, expression of the serine 897 phosphorylated EphA2 and expression of MT1-MMP showed the same localization.

Figure 13:
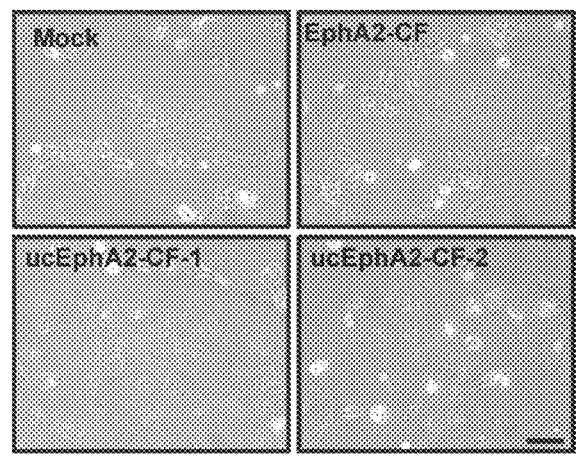

FIG. 13 shows the results of expressing, in A431 cells, an EphA2 mutant having resistance against cleavage by MT1-MMP. Mock represents a cell not expressing EphA2, EphA2-CF is a cell expressing normal EphA2, and ucEphA2-CF-1 and ucEphA2-CF-2 represent cells expressing an EphA2 mutant having resistance to cleavage by MT1-MMP. The A431 cells have a spindle-shaped phenotype peculiar to malignant cancer cells (Mock and EphA2-CF), but cells expressing a mutant having resistance to cleavage by MT1-MMP changed to a normal epithelial cell phenotype.

Figure 14:
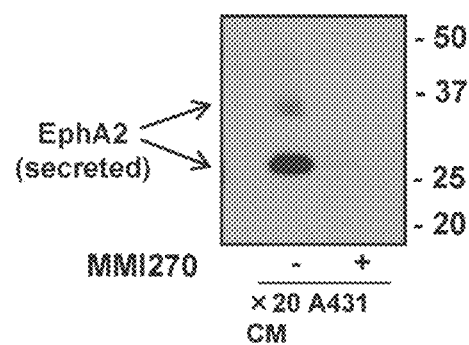

FIG. 14 shows the results of detecting, by western blotting, a fragment obtained by expressing EphA2 in A431 cells and cleaving it by endogenous MT1-MMP.

EMBODIMENT FOR CARRYING OUT THE INVENTION

[Testing Method of Cancer]

The cancer testing method of the present invention comprises a step of measuring the amount of an EphA2 protein fragment having a molecular weight of from 30 kDa to 80 kDa in a sample obtained from a subject.

In the carcinoma tissue, expression of a protease such as MT1-MMP has been enhanced and EphA2 is processed by it. It is therefore possible to examine cancer by detecting such a processed fragment from a sample obtained from a subject.

The EphA2 protein fragment to be measured by the cancer testing method of the present invention may be any fragment insofar as it is a fragment having a molecular weight of from 30 kDa to 80 kDa.

In one embodiment of the cancer testing method of the present invention, an amount of an N-terminal-comprising EphA2 protein fragment having a molecular weight of from 30 kDa to 80 kDa may be measured.

In another embodiment of the cancer testing method of the present invention, an amount of at least one of the following fragments (i) to (iii) may be measured:

(i) a peptide having any one of the amino acid sequences set forth in SEQ ID NO: 1 to 4;

(ii) a peptide having an amino acid sequence obtained by adding, substituting, or deleting one or more amino acids from any one of the amino acid sequences set forth in SEQ ID NO: 1 to 4; and (iii) a peptide having an amino acid sequence having 80% or more sequence identity with any one of the amino acid sequences set forth in SEQ ID NO: 1 to 4.

The peptide represented by SEQ ID NO: 1 is an N terminal side fragment of EphA2 protein represented by SEQ ID NO: 5 obtained as a result of cleavage between S431 and V432, and SEQ ID NO: 2 represents a fragment obtained simultaneously on the C terminal side.

The peptide represented by SEQ ID NO: 3 is an N terminal side fragment obtained as a result of cleavage between 1434 and N435, and SEQ ID NO: 4 represents a fragment obtained simultaneously on the C terminal side.

The peptide having any one of the amino acid sequences set forth in SEQ ID NO: 1 to 4 is a fragment produced through processing of EphA2 by MT1-MMP. The present inventors have found that as shown in FIG. 10, when MT1-MMP expression is enhanced with progression of canceration of cells and a ligand-binding domain is released from EphA2 to convert EphA2 into a ligand-insensitive RTK, ligand-independent EphA2 action then activates each signaling pathway to control cells to promote growth, survival, and migration and contributes to acquisition of a malignant phenotype of cancer cells.

The canceration degree of cells can therefore be determined by measuring the amount of the peptide having any one of the amino acid sequences set forth in SEQ ID NO: 1 to 4 in a sample obtained from a subject.

The fragments represented by SEQ ID NO: 2 and 4 are fragments containing a transmembrane region (TM) and they may be called "stud" herein.

In the cancer testing method of the present invention, any of the fragments represented by SEQ ID NO: 1 to 4 may be measured. Two or more of them may be measured. The method facilitates detection of a fragment represented by SEQ ID NO: 1 or 2 which is a free fragment.

In the cancer testing method of the present invention, not only an amount of (i) a peptide having any one of the amino sequences set forth in SEQ ID NO: 1 to 4 but also an amount of (ii) a peptide obtained by adding, substituting, or deleting one or more amino acids from any one of the amino acid sequences set forth in SEQ ID NO: 1 to 4 or (iii) a peptide having an amino acid sequence having 80% or more sequence identity with any one of the amino acid sequences set forth in SEQ ID NO: 1 to 4 may be measured. Alternatively, a combination of some of the above-mentioned peptides may be measured.

The peptide (ii) having an amino acid sequence obtained by adding, substituting, or deleting one or more amino acids from any one of the amino acid sequence set forth in SEQ ID NO: 1 to 4 or the peptide (iii) having an amino acid sequence having 80% or more sequence identity with any one of the amino acid sequence set forth in SEQ ID NO: 1 to 4 may be produced as a processed fragment, for example, when EphA2 contains mutation not having resistance against processing by MT1-MMP.

When the term "amino acid sequence obtained by adding, substituting, or deleting one or more amino acids" is used herein, the number of amino acids added, substituted, or deleted is not particularly limited and examples include one, two, three, four, five, six, seven, eight, nine, and ten amino acids. The addition, substitution, or deletion position may be either at the end or middle of the peptide and may be one position or two or more positions.

When the term "amino acid sequence having 80% or more sequence identity" is used herein, the sequence identity may be any % insofar as it is 80% or more. Examples include 80%, 85%, 90%, 95%, and 98%.

Peptides which belong to (i) to (iii) and are EphA2 protein fragments having a molecular weight of from 30 kDA to 80 kDA in a sample obtained from a subject may hereinafter be called "peptides of the present invention", collectively.

The step of "measuring the amount of a protein fragment" described herein includes not only quantifying the fragment actually but also detecting presence or absence of the fragment or measuring and comparing the amount of the fragment in the sample collected at a plurality of time points to study a time dependent change.

Measurement of the amount of the fragment in the testing method according to the present invention can be carried out using any method capable of detecting a fragment in a sample. Examples include, but not limited to, immunoassay (including aggregation method and turbidimetric method), Western blotting, and surface plasmon resonance (SPR) method.

For example, immunoassay using an antibody against the EphA2 fragment is convenient and preferable.

The "antibody against the EphA2 fragment" described herein may be any antibody insofar as it is capable of specifically recognizing the above-mentioned EphA2 fragment. Examples include the following antibodies:

(1) antibodies capable of specifically recognizing a fragment of EphA2 protein having a molecular weight of from 30 kDa to 80 kDa, (2) antibodies capable of specifically recognizing a fragment which is a fragment of EphA2 protein having a molecular weight of from 30 kDa to 80 kDa and contains the N terminal of EphA2, (3) antibodies capable of specifically recognizing a peptide corresponding to any of the above-mentioned (i) to (iii), and (4) antibodies having an epitope in a cysteine-rich domain (Cysteine rich domain; CRD, from about position 180 to position 340) of an amino acid sequence of EphA2 represented by SEQ ID NO: 5.

The above-mentioned antibodies (1) to (3) can be prepared by those skilled in the art in a known manner. For example, they may be prepared in a manner known per se in the art by immunizing a non-human animal with the EphA2 fragments specified in (1) to (3), respectively. Alternatively, they may be prepared by immunizing a non-human animal with full-length EphA2 and then screening, in a manner known per se in the art, antibodies that bind to the respective fragments specified in (1) to (3) from the antibodies thus obtained, The antibodies (4) can also be prepared by those skilled in the art in a known manner. For example, they may be prepared by immunizing a non-human animal with a peptide containing an epitope sequence. Alternatively, an epitope-sequence-containing peptide is immobilized onto a solid phase support and an antibody that binds to the epitope may be selected from an antibody library or an antibody fragment library constructed by phage display or the like. The cysteine-rich domain can be located, for example, at from position 180 to position 340 or at from position 201 to position 314 of the amino acid sequence set forth in SEQ ID NO: 5.

Immunoassay is performed using an antibody against the EphA2 fragment of the present invention labeled to permit detection or an antibody (secondary antibody) against an antibody against the EphA2 fragment of the present invention labeled to permit detection. It is classified, by an antibody labeling method, into enzyme immunoassay (EIA, ELISA, or ELISOPT), radioimmunoassay (RIA), fluorescence immunoassay (FIA), fluorescence polarization immunoassay (FPIA), chemiluminescence immunoassay (CLIA), and the like and any of them is usable in the method of the present invention.

In ELISA, an antibody labeled with an enzyme such as peroxidase and alkaline phosphatase is used: in RIA, that labeled with a radioactive substance such as $^{125}$I, $^{131}$I, $^{35}$S, and $^{3}$H is used; in FPIA, that labeled with a fluorescent substance such as fluorescein isothiocyanate, rhodamine, dansyl chloride, phycoerythrin, tetramethylrhodamine isothiocyanate, and near-infrared fluorescent material is used; and in CLIA, that labeled with a luminescent substance such as luciferase, luciferin, and aequorin is used. In addition, an antibody labeled with nanoparticles such as colloidal gold or quantum dot can be detected.

In immunoassay, detection may also be carried out by labeling the antibody against the EphA2 fragment of the present invention with biotin and then binding avidin or streptavidin labeled with an enzyme or the like to the antibody.

Among immunoassays, ELISA using enzyme labeling is preferred because a target peptide can be measured conveniently and speedily.

ELISA has competitive assay and sandwich assay. In the competitive assay, an antibody against the EphA2 fragment of the present invention is immobilized onto a solid phase support such as microplate and then a sample is added to cause an antigen antibody reaction. After washing, the sample is reacted with an enzyme substrate to cause color development and an absorbance is measured. The sample containing a large amount of the EphA2 fragment of the present invention shows weak color development, while that containing a small amount shows strong color development so that the amount of the EphA2 fragment can be determined using a calibration curve.

In the sandwich assay, after an antibody against the EphA2 fragment of the present invention is immobilized onto a solid phase support and a sample is added to cause a reaction therebetween, another enzyme-labeled antibody against the EphA2 fragment of the present invention capable of recognizing an epitope is added to cause a reaction therebetween. After washing, reaction with an enzyme substrate, and color development, an absorbance is measured. In such a manner, the amount of the EphA2 fragment of the present invention can be determined. Alternatively, in the sandwich assay, it is also possible to, after reaction between an antibody immobilized onto a solid phase support and a sample, add a non-labeled antibody (primary antibody) and then add an antibody (secondary antibody) against this non-labeled antibody after labeling it with an enzyme.

When the enzyme is a peroxidase, examples of the enzyme substrate usable here include 3,3'-diaminobenzidine (DAB), 3,3'5,5'-tetramethylbenzidine (TMB), and o-phenylenediamine (OPD). When the enzyme is an alkaline phosphatase, examples include p-nitropheny phosphate (NPP).

The "solid phase support" described herein is not particularly limited insofar as it permits immobilization of an antibody thereonto. Examples include microtiter plates, substrates, and beads made of glass, a metal, a resin, or the like, nitrocellulose membranes, nylon membranes, and PVDF membranes. The target substance can be immobilized onto such a solid phase support in a known manner.

The antibody against the EphA2 fragment of the present invention can be prepared in a known manner whether it is a monoclonal antibody or a polyclonal antibody. A monoclonal antibody can be obtained, for example, by isolating antibody producing cells from a non-human mammary animal immunized with any of the peptides of the present invention, fusing the antibody producing cells with myeloma cells or the like to prepare a hybridoma, and purifying an antibody produced by this hybridoma. A polyclonal antibody can be obtained from the serum of an animal immunized with the peptide of the present invention.

As the antibody against the EphA2 fragment of the present invention, an existing antibody may be used instead.

Examples of the sample obtained from a subject and used in the testing method of the present invention include body fluids such as blood, lymph, and urine, feces, and lysates of cells or tissues. They can be used after treated by a method suited for the measuring method of a peptide amount.

The free fragment represented by SEQ ID NO: 1 or 3 can be detected easily from body fluids such as blood, lymph, and urine, feces, and the like. The stud fragment represented by SEQ ID NO: 2 or 4 can be detected after the lysates of cells or tissues are treated with a buffer containing a highly soluble surfactant (such as RIPA).

The term "cancer" is used herein in the broadest meaning. Examples of the cancer include, but not limited to, brain tumor, head and neck cancer, esophageal cancer, gastric cancer, colon cancer, anal cancer, rectal cancer, liver cancer, hepatoma, kidney cancer, renal cell carcinoma, lung cancer, non-small cell lung cancer, osteosarcoma, gallbladder cancer, pancreatic cancer, breast cancer, endometrial cancer, cervical cancer, prostatic cancer, testicular cancer, bladder cancer, and skin cancer.

The testing method of the present invention is particularly useful for cancer in which EphA2 is expressed. Whether EphA2 is expressed in cancer cells or not can easily be confirmed by those skilled in the art. Examples of such cancers include breast cancer, liver cancer, prostatic cancer, glioma, melanoma, ovarian adenocarcinoma, esophageal cancer, urinary tract cancers (bladder cancer, renal pelvis cancer), pancreatic cancer, lung cancer, gastric cancer, and colon cancer.

The "method of testing or testing method" described herein means testing of a sample collected from a subject in order to obtain information necessary for diagnosis. The testing method of the present invention is carried out, for example, in an testing company.

The "method of testing cancer or cancer testing method" described herein means testing cancer and all the phenomena caused thereby, for example, testing a sample collected from a subject in order to obtain information necessary for determining presence or absence of the cancer, stage, malignancy, stop or delay of progress, presence or absence of metastasis, or presence or absence of a therapeutic effect.

The "method of testing cancer or cancer testing method" described herein may be used in so-called companion diagnostics which is performed so as to know the effect or side effect of an anticancer agent in advance. The "anticancer agent" is not particularly limited but examples include anticancer agents targeting, for example, EphA2, MT1-MMP, or a downstream signal of EphA2 to be activated in a ligand-independent manner. When the amount of the EphA2 fragment is significantly larger than that of able-bodied persons or patients suffering from another cancer, an anticancer agent targeting them is presumed to be effective.

[Testing Kit for Cancer]

The testing kit for cancer according to the present invention is a kit for testing cancer by using the above-mentioned testing method and it includes the "antibody against an EphA2 fragment" of the present invention.

The testing kit of the present invention includes a reagent and apparatus necessary for measuring an amount of the peptide of the present invention by immunoassay making use of an antigen antibody reaction between the antibody against the EphA2 fragment of the present invention and the EphA2 fragment of the present invention.

An testing kit according to one embodiment is for measuring the amount of the EphA2 fragment of the present invention by sandwich assay and it includes a microtiter plate, a capturing antibody against the EphA2 fragment of the present invention, an antibody against the EphA2 fragment of the present invention labeled with an alkaline phosphatase or peroxidase; and an alkaline phosphatase substrate (NPP, or the like) or a peroxidase substrate (DAB, TMB, OPD, etc.). The capturing antibody and the labeled antibody recognize respectively different epitopes.

Such a kit is used in the following manner: first, a capturing antibody is immobilized onto a microtiter plate. A sample treated as needed is then added to the microtiter plate, followed by incubation, removal of the sample, and washing. Then, a labeled antibody is added and the plate is incubated. A substrate is added for color development. By analyzing color development by using a microtiter plate reader or the like, the amount of the EphA2 fragment of the present invention can be determined.

The testing kit according to another embodiment is for measuring an amount of the EphA2 fragment of the present invention by the sandwich assay while using a secondary antibody. It includes a microplate, a capturing antibody against the EphA2 fragment of the present invention, an antibody, as a primary antibody, against the EphA2 fragment of the present invention, an antibody, as a secondary antibody, against the EphA2 fragment of the present invention, labeled with an alkaline phosphatase or peroxidase, and a substrate of the alkali phosphatase (NPP or the like) or peroxidase (DAB, TMB, OPD, or the like).

The capturing antibody and the primary antibody recognize respectively different epitopes.

In such a kit, first, the capturing antibody is immobilized onto a microtiter plate. A sample treated as needed is then added to the resulting microtiter plate, followed by incubation, removal of the sample, and washing. After addition of the primary antibody, incubation and washing are carried out. Further, the enzyme-labeled secondary antibody is added. After incubation, a substrate was added to cause color development. The amount of the EphA2 fragment of the present invention can be determined by measuring the color development by using a microtiter plate reader or the like. Using the secondary antibody can amplify the reaction and enhance the detection sensitivity.

The testing kit according to the present invention may further include a buffer, an enzymatic reaction stop solution, a microplate reader, and the like necessary for the testing.

The labeled antibody is not limited to an enzyme-labeled antibody and it may be an antibody labeled with a radioactive substance (such as $^{25}$I, $^{131}$I, $^{35}$S, or $^{3}$H), a fluorescent substance (such as fluorescein isothiocyanate, rhodamine, dansyl chloride, phycoerythrin, tetramethylrhodamine isothiocyanate, or near-infrared fluorescent material), a luminescent substance (such as luciferase, luciferin, or aequorin), or nanoparticles (colloidal gold, quantum dot). In addition, a biotinylated antibody may be used as the labeled antibody and the kit may include labeled avidin or streptavidin.

The kit may include a plurality of antibodies against the EphA2 fragment of the present invention.

[Screening Method of Anticancer Agents]

The screening method of an anticancer agent according to the present invention includes:

a step of culturing cells expressing EphA2 under conditions under which MT1-MMP processes EphA2, a step of adding a test compound to a culture medium of the cells and incubating in the presence of MT1-MMP, and a step of determining presence or absence of the processing of EphA2.

As the cells expressing EphA2, existing cultured cancer cells may be used. Alternatively, they may be prepared by selecting proper cells and forcibly expressing the protein of them. The forced expression may be performed, for example, by the method used in Examples of the present invention but those skilled in the art can achieve it as needed by a known method or a method equivalent thereto.

In the "step of incubating in the presence of MT1-MMP", MT1-MMP may be co-expressed in the cells expressing EphA2 or they may be expressed in difference cells, followed by coculturing. Alternatively, MT1-MMP prepared separately may be added to the culture medium. As the conditions under which EphA2 is processed by MT1-MMP, culturing conditions used in Examples of the present invention may be used. The conditions are however not limited thereto and can be selected as needed by those skilled in the art.

The test compound is not particularly limited and any substance is usable. Examples include low molecular compounds, high molecular compounds, nucleic acids, peptides, proteins, sugars, and lipids. The concentration of the test compound or incubation conditions can be determined by those skilled in the art according to the test compound.

The step of determining presence or absence of the processing of EphA2 can be carried out, for example, by using the above-mentioned method of measuring the amount of a peptide of the present invention. In this step, the test compound that reduces processing compared with processing when it is absent can be selected as an anticancer agent candidate.

[Method for Diagnosing Cancer]

The present invention also provides a method for diagnosing cancer. The method for diagnosing cancer means that based on the results obtained by the testing method of the present invention, doctors or the like determine presence or absence of the cancer, stage, malignancy, stop or delay of progress, presence or absence of metastasis, or presence or absence of a therapeutic effect.

[Anticancer Agent]

The anticancer agent of the present invention contains an siRNA having the following sequence or a precursor thereof, or a nucleic acid encoding them.

```
siRNA #1
                                    (SEQ ID NO: 6)
    S: ggauggacacggagaauuutt (SEQ ID NO: 7)
    AS: aaauucuccguguccaucctt siRNA #2
                                    (SEQ ID NO: 8)
    S: gcgaugaagucuucacuuatt (SEQ ID NO: 9)
    AS: uaagugaagacuucaucgctt siRNA #3
                                    (SEQ ID NO: 10)
    S: ggguagagacccugagacatt (SEQ ID NO: 11)
    AS: ugucucagggucucuaccctt
```

The siRNA is a double stranded RNA having usually from about 19 to 31 bases, for example, from about 21 bases to 25 bases. In general, one of the strands has a base sequence complementary to a portion of the target mRNA and the other one has a complementary sequence thereto, but it is not required to be completely complementary to the target mRNA.

RNAi which is an expression inhibition method using an siRNA is a sequence-specific gene expression control mechanism induced from a double-stranded nucleic acid. It is a method making use of a gene expression control mechanism originally present in the living body and the siRNA used in this method has high target specificity so that it has high safety.

The siRNA has, as a typical structure, a double-stranded RNA having 21 base pairs and has, at the 3' portion of the RNA strand thereof, two overhanging bases. The siRNA is produced by cutting by Dicer from a hairpin type RNA (shRNA) or longer double-stranded RNA. The shRNA or longer double-stranded RNA before cutting by Dicer can be used for the anticancer agent of the present invention as a precursor of the siRNA.

The siRNA can be designed by a known method based on the base sequence of a target mRNA. The siRNA may be either a double stranded RNA or a DNA-RNA chimeric double-stranded nucleic acid, or an artificial nucleic acid or a nucleic acid subjected to various modifications insofar as it has an RNAi effect on the target mRNA.

The anticancer agent of the present invention embraces a nucleic acid to be transcribed to an siRNA or a precursor thereof in a cell.

Disclosure of all the patent documents and non-patent documents cited herein is incorporated herein by reference in its entirety.

Examples

The present invention will hereinafter be described specifically based on Examples, but the present invention is not limited to or by them. Those skilled in the art can change the present invention into various embodiments without departing from the significance of the present invention. Such a change is also embraced within the scope of the present invention.

Figure 1B:
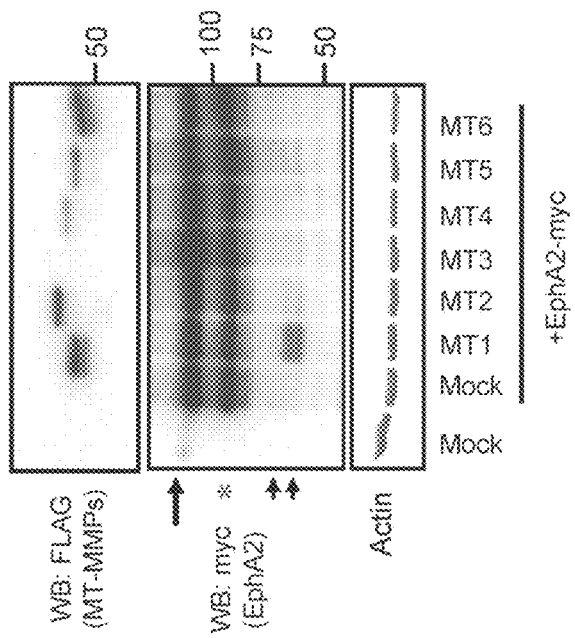
FIG. 1B shows the results of verifying, by western blotting, whether processing of EphA2 occurs or not by various membrane type MMPs. When EphA2 having a Myc-labeled C terminal and MT1-MMP to MT6-MMP were forcibly expressed in HT1080 cells, respectively, a processed fragment of EphA2 (small arrow) was detected only in the MT1-MMP-introduced cells. This has suggested that MT1-MMP is a main membrane type MMP for processing of EphA2. Indicated by "*" is a non-specific band.

1. Preparation of Transfectant (FIG. 1)

HT1080 cells expressing c-myc-EphA2 stably were prepared by a ViraPower™ lentiviral expression system using a plenti-c-myc-EphA2 vector in HT1080 and expression vectors (pSG-MT1-6-MMPs) of MT1-6-MMPs were transiently introduced into the resulting cells. EphA2 and MT1-MMP were detected by western blotting using an anti-Myc polyclonal antibody and an anti-MT1-MMP monoclonal antibody. Respective expression vectors of the MT-MMPs were introduced using FuGene6 (Rhoche). Expression of c-myc-EphA2 and wild type MT1-MMP was confirmed by solubilizing each of the cells (10 cm) by RIPA and then performing immunoprecipitation (IP) of EphA2 and stud thereof by an anti C-myc antibody. In order to inhibit the protease activity of MT1-MMP, BB94 or TIMP-2 was added as an MMP inhibitor to a culture solution.

Figure 1A:
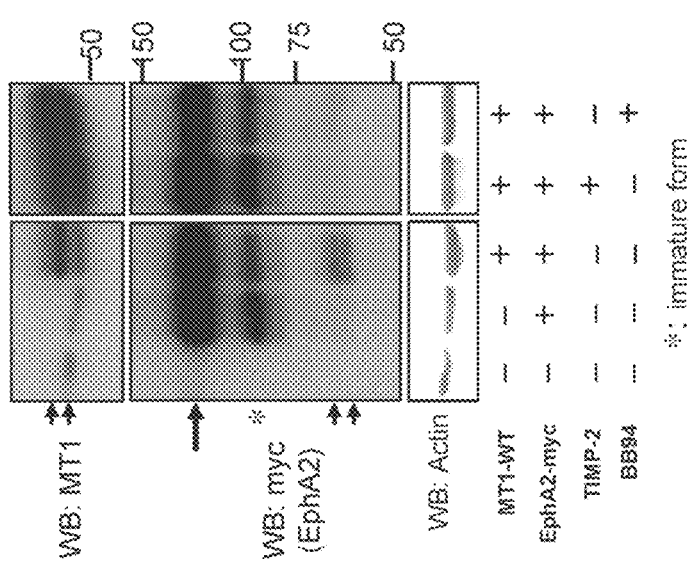
FIG. 1A shows the results of introducing MT1-MMP and EphA2 having Myc-labeled C-terminal into human fibrosarcoma HT1080 cells and detecting an EphA2 stud by western blotting with Myc antibody. From the HT1080 cells in which MT1-MMP is forcibly expressed, full-length type EphA2 (large arrow) and respective EphA2 processed fragments (small arrow) having a molecular weight of 65 and 60 kDa were detected. When the cells were treated with TIMP-2 and BB94 which are inhibitors of MT1-MMP, the activity of MT1-MMP was inhibited and thereby production of these processed fragments was suppressed.

As shown in FIG. 1A, from the HT1080 cells forcibly expressing MT1-MMP, full-length type EphA2 (large arrow) and respective EphA2 processed fragments (small arrow) having a molecular weight of 65 and 60 kDa were detected. When the cells were treated with TIMP-2 and BB94 which were MT1-MMP inhibitors, the activity of MT1-MMP was inhibited and thereby, production of these processed fragments was suppressed.

As shown in 1B, when EphA2 having a Myc-labeled C terminal and MT1 to MT6-MMPs were forcibly expressed in HT1080 cells, respectively, a processed fragment of EphA2 (small arrow) was detected only in the MT1-MMP-introduced cells. This has suggested that MT1-MMP is a main membrane type MMP for processing of EphA2.

The purified 65 and 60 kDa processed fragments were identified by analyzing a purified protein (50 pmole) respectively thereof by Edman degradation method using an ABI peptide sequencer (Procise 494 HT) and thereby determining five residues counted from the N terminal (consigned to APRO science). The results are shown in FIG. 1C. The 65-kDa Fragment A had VSINQ as an N terminal sequence and the 60-kDa Fragment B had NQTEPP as an N terminal sequence.

In order to identify the cleavage site of EphA2 by MT1-MMP, a peptide chain containing the cleavage site found in FIG. 1C was synthesized and was subjected to in vitro digestion with a recombinant protein of MT1-MMP. The results are shown in FIG. 1D. In in vitro digestion, MT1-MMP cleaved two sites (arrows) between S426 and F427 and between 431S and 432V, each of the EphA2 peptide. The results of FIGS. 1C and 1D have suggested that MT1-MMP cleaved between 431-S and 432-V on the cell membrane and in conjunction with this cleavage, an unknown protease cleaved between 434-I and 435-N.

Figure 1E:
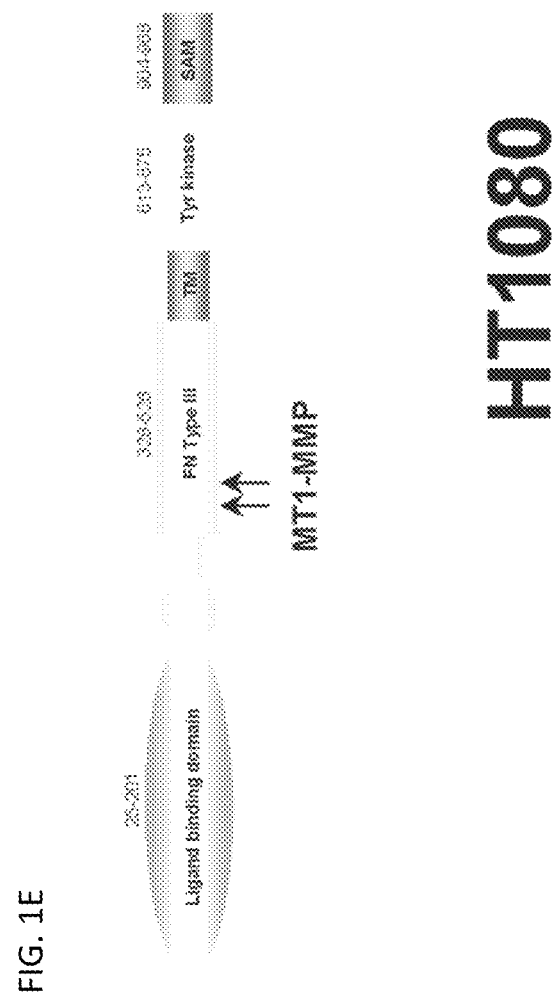
FIG. 1E is a schematic view showing the cleavage site of EphA2 by MT1-MMP. This has revealed that the cleavage site is a fibronectin site and by this processing, a ligand-binding domain is released.

FIG. 1E is a schematic view showing the cleavage site of EphA2 by MT1-MMP. This has revealed that the cleavage site is a fibronectin site and by this processing, a ligand-binding domain is released.

2. MT1-MMP Knockdown (FIG. 2)

With regard to MT1-MMP knockdown, MT1-MMP expression was knocked down using two triomix siRNAs (three different siRNAs, product of B-bridge) specific to MT1-MMP.

```
siRNA #1
                              (SEQ ID NO: 6)
S:  ggauggacacggagaauuutt (SEQ ID NO: 7)
AS: aaauucccguguccaucctt siRNA #2
                              (SEQ ID NO: 8)
S:  gcgaugaagucuuucacuuatt (SEQ ID NO: 9)
AS: uaagugaagacuucaucgctt siRNA #3
                              (SEQ ID NO: 10)
S:  ggguagagacccugagacatt (SEQ ID NO: 11)
AS: ugucucagggucucuaccctt
```

2-1. Detection of EphA2 and Stud Thereof (FIGS. 2A to 2D)

A431 cells were solubilized with RIPA, EphA2 and a stud thereof in the lysate were immunoprecipitated with an anti-EphA2 antibody (recognizes the intracellular domain of the C terminal, product of Santa Cruz), and the immunoprecipitated fraction was western blotted with the same EphA2 antibody and an anti-tyrosine phosphorylation antibody (4G10, product of Millipore) (A, EphA2, p-EphA2). As a negative control, on the other hand, expression of E-cadherin was studied by western blotting using an anti-E-cadherin monoclonal antibody (product of Merck).

Figure 2B:
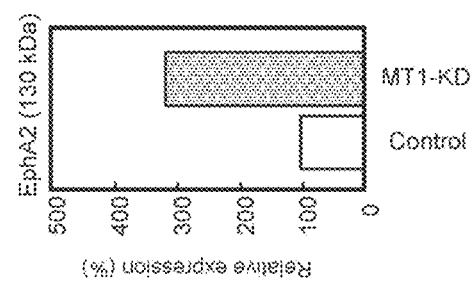
FIGS. 2B, 2C, and 2D show the results of relative expression of EphA2, E-cadherin, and phosphorylated EphA2 determined based on the results of FIG. 2A. The 65-kDa and 60-kDa processed fragments of EphA2 disappeared by MT1-MMP knockdown (FIG. 2A). On the other hand, presence or absence of the expression of MT1-MMP caused no change in processing of E-cadherin (FIGS. 2A, 2C).
Figure 2A:
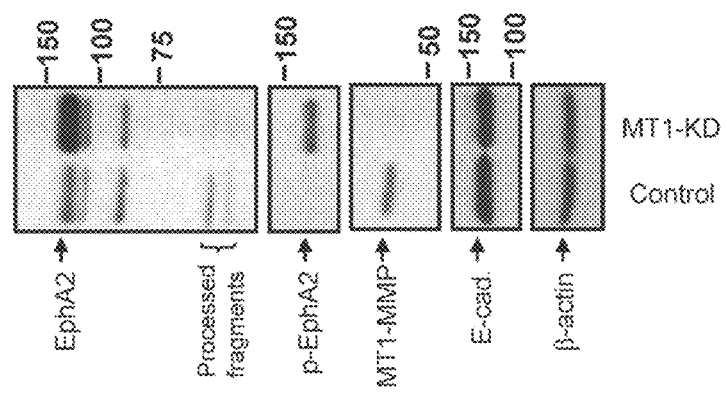
FIG. 2A shows the results of immunoprecipitating, with an antibody against the C terminal of EphA2, a lysate of cells whose MT1-MMP expression has disappeared as a result of siRNA treatment and western blotting the precipitate with the same antibody and an anti-tyrosine phosphorylation antibody (FIG. 2A, EphA2, p-EphA2).
Figure 2D:
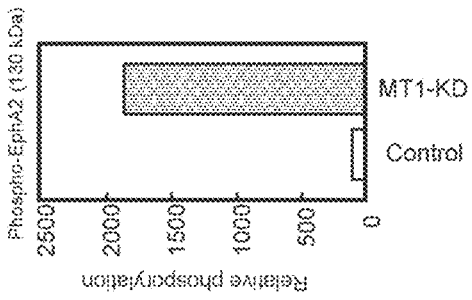
Figure 2C:
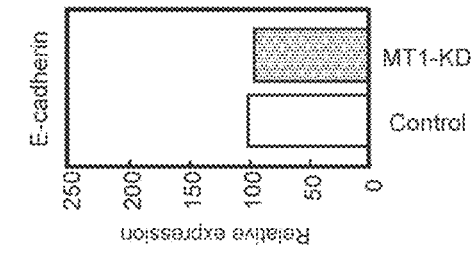

The results are shown in FIG. 2A. FIGS. 2B to 2D show the results of relative expression of EphA2, E-cadherin, and phosphorylated EphA2 determined based on the results of FIG. 2A. Due to MT1-MMP knockdown, the 65-kDa and 60-kDa processed fragments of EphA2 disappeared (A). On the other hand, presence or absence of MT1-MMP expression caused no change in the processing of E-cadherin (A, C).

Figure 2G:
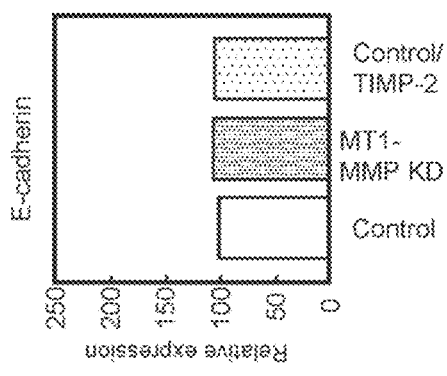

2-2. Detection of EphA2 and Stud Thereof in Cell Surface Layer (FIGS. 2E to 2G)

In order to study the processing of EphA2 of the cell surface layer, the membrane protein of A431 cells was labeled with LC-biotin (Pierce) and the membrane protein was purified by pulldown with avidin beads (Immobilized Streptavidin, Pierce). An EphA2 amount in the purified membrane protein was compared by western blotting with an anti-EphA2 antibody. Comparison among the proteins was made based on densitograph using Image-J.

The results are shown in FIG. 2E. FIGS. 2F and 2G show the results of relative expression of EphA2 and E-cadherin determined based on the results of FIG. 2E. Due to MT1-MMP knockdown, an amount of full-length EphA2 increased and the results are similar even after treatment with TIMP-2 (E, F). On the other hand, no change in the expression amount of E-cadherin in the cell surface layer was found whether the expression of MT1-MMP was present or not (E, G).

3-1. Detection of Phosphorylation of EphA2, Eric, and Akt (FIG. 3A to 3F)

A dephosphorylation enzyme inhibitor (sodium orthovanadate (V), sodium fluoride) was added to RIPA and the cells were each solubilized with the resulting mixture. IP with an antibody capable of recognizing the C terminal of EphA2 was performed and EphA2 and p-EphA2 were detected by western (IP-western) with an anti-EphA2 antibody and an anti-tyrosine phosphorylation antibody (4G10). Further, p-Erk1/2, Erk1/2, p-Akt, and Akt were detected by western blotting using antibodies specific thereto, respectively. With regard to a phosphorylation ratio, a band obtained by western blotting was quantified by densitometry with Image J.

As the antibodies, used were: anti-p-Erk1/2 monoclonal antibody (Santa Cruz), anti-Erk1/2 polyclonal antibody (Santa Cruz), anti-p-Akt (Ser473) monoclonal antibody (Cell Signaling), and anti-Akt (Ser473) monoclonal antibody (Cell Signaling).

The results are shown in FIGS. 3A to 3F. A similar experiment was performed using human heat and neck cancer SCC61 cells. The results are shown in FIG. 7.

In the presence of Ephrin-A1, presence or absence of MT1-MMP expression had no influence on the activation of the EGF receptor (A, B). The MT1-MMP knockdown enhanced phosphorylation of EphA2 itself (A, C). Erk1/2 and Akt activities induced by EGF in the presence of Ephrin-A1 were significantly suppressed by MT1-MMP knockdown (A, D, E). Similar results were found in human breast cancer BT549 cells and head and neck cancer SCC61 cells (F, FIG. 7), but were found in none of ovarian carcinoma IGROV-1 cells and breast cancer BT-20 cells that did not express EphA2, and MDA-MB-231 cells having k-ras mutation (F).

3-2. Cell Growth Assay (Two-Dimensional and Three-Dimensional Culture, Spheroid Formation) (FIGS. 3G to 3I)
(Two-Dimensional Culture)

Wild type and MT1-MMP knockdown A431 cells were seeded on culture dishes (two-dimensional culture) ($8\times10^3$ cells/2 ml/6 well plate), respectively, and cultured for four days in a DMEM/1% FCS culture solution. The number of cells was counted using a hemocytometer.
(Three-Dimensional Culture)

Collagen I gel (3 mg/ml, Nitta Gelatin) extracted in acetic acid, a neutralization buffer (50 mM NaOH, 260 mM NaHCO3, 200 mM HEPES), and each of the two types of cells were mixed and the resulting mixture was seeded to satisfy $2.5\times10^4$/250 µl/48 well plate. After completion of the polymerization of the collagen gel, they were cultured for 7 days in 400 µl/well of a DMEM/1% FCS culture solution. After culturing, the collagen gel was dissolved with 0.1% collagenase. The cells were treated with trypsin to dissociate them into single cells and the number of the cells was counted using a Coulter counter.
(Spheroid Formation)

The two types of the cells were each detached with trypsin from one another and the number of the cells was counted by a hemocytometer. They were seeded in a low adhesion plate (PrimeSurface (registered trademark), Sumitomo Bakelite) of each cell protein (100 cells/100 µl/96 well plate) and cultured for 7 days in a DMEM/1% FCS culture solution. The number of spheroid formation cells was obtained from their volume (½×long diameter×(short diameter)$^2$).

The results are shown in FIGS. 3G to 3I. Under the conditions of the two-dimensional culture dish, no influence of the presence or absence of MT1-MMP on the Ephrin-A1/EphA2-dependent cell growth inhibition was observed (G, H). However, in the three-dimensional culture in the collagen gel and anchorage-independent spheroid formation, growth of MT1-MMP knockdown cells was significantly suppressed in an Ephrin-A1-dependent manner (I).

4. Measurement of RhoG Activity (FIG. 4)

By using A431 cells whose MT1-MMP expression was knocked down by siRNA, an influence of Ephrin-A1-dependent EphA2 on an RhoG signaling downstream of the EGF receptor was studied.

A fusion protein of ELMO2 and GST, each serving as an effector of RhoG, was solid phased on glutathione beads and the RhoG activity in a cell suspension solubilized with RIPA was detected by pull-down using ELMO2/GST beads as a bait. Co-precipitated RhoG was detected using an anti-RhoG polyclonal antibody (Santa Cruz) and the RhoG activity was quantified by densitometry with Image J. An expression vector of ELMO2 was kindly given by Chihiro Sasakawa, professor of Division of Bacterial Infection, Medical Institute of Science, The University of Tokyo.

The results are shown in FIG. 4. No RhoG activity was detected from the cells not treated with EGF (A). After EGF stimulation, on the other hand, the MT1-MMP knockdown cells showed a significant decrease in RhoG activity by the treatment with Ephrin-A1 (A, B). Similar results were found in the SCC61 cells (C). Study of the migration activity of the EGF-stimulated cells in a transwell chamber has revealed that Ephrin-A1 treatment significantly suppressed cell migration in the MT1-MMP knockdown cells (D, E). This has suggested that processing of EphA2 by MT1-MMP has a role of enhancing a small GTPase activity.

5-1. Preparation of Mutant Resistant to MT1-MMP Processing (FIGS. 5A to 5D)

Figure 5A:
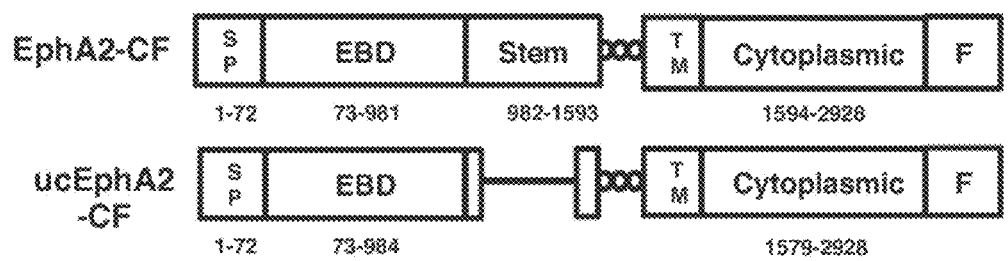
Figure 5B:
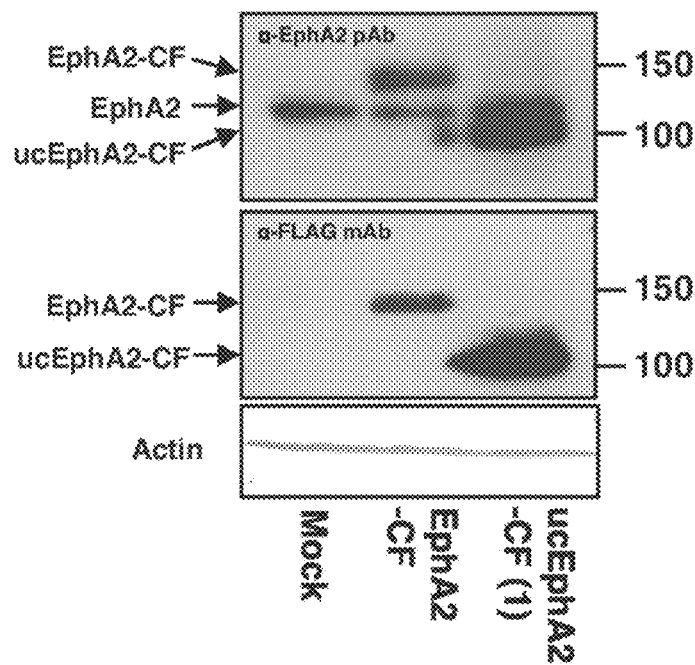
Figure 5C:
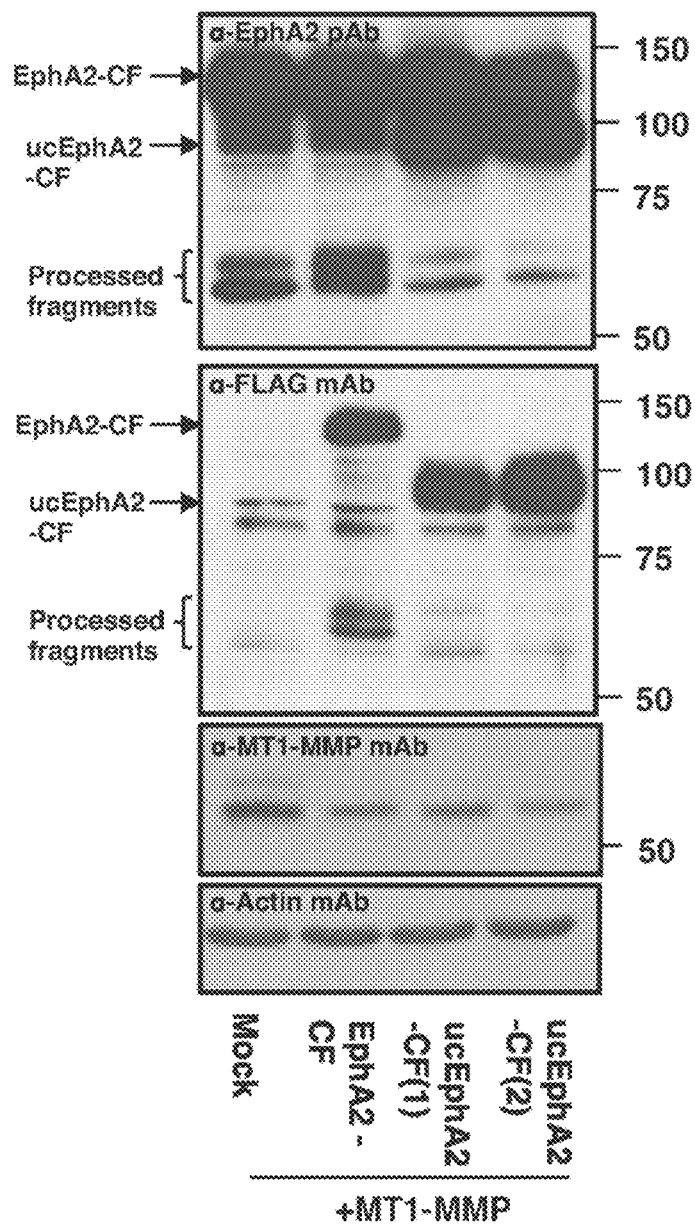
Figure 5D:
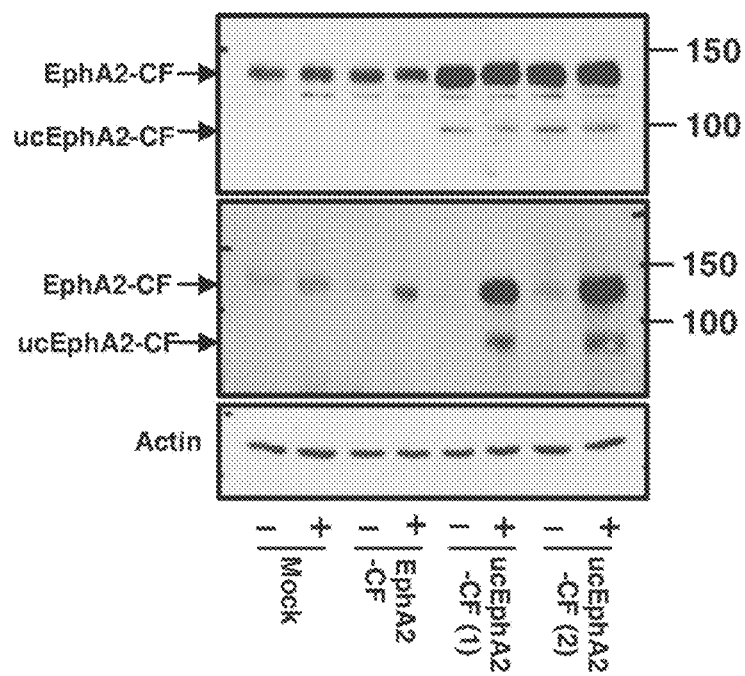
Figure 5E:
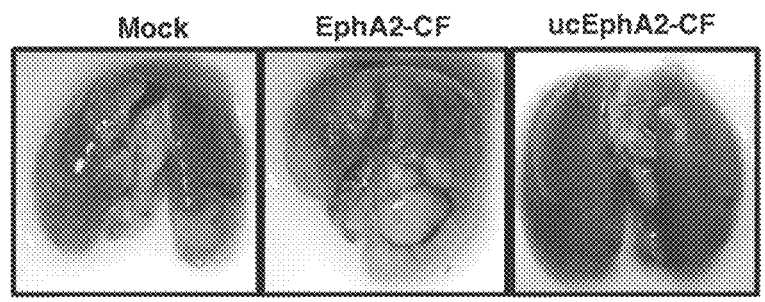
Figure 5F:
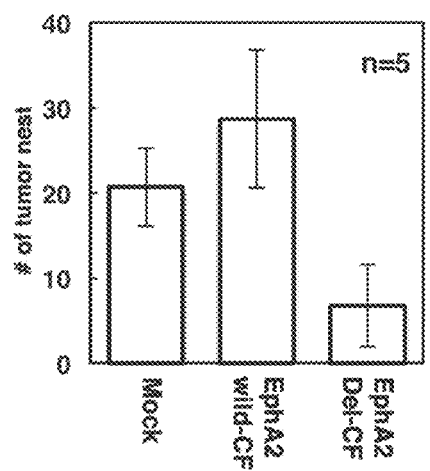
Figure 5G:
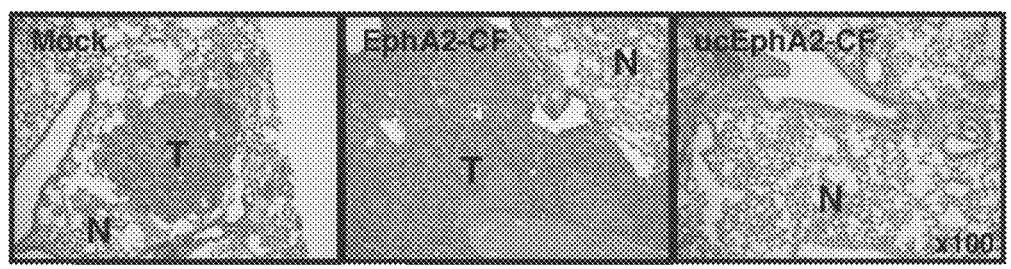

Expression vectors of MOCK, wild type, and EphA2 deleted at a site to be processed by MT1-MMP and having a FLAG-labeled C terminal were constructed and an expression gene was introduced into A431 cells by using a ViraPower™ lentiviral expression system (FIGS. 5A, 5B). Expression proteins were each confirmed by detecting expression of EphA2 in a cell suspension solubilized with RIPA by western blotting using an anti-FLAG antibody (M2) and an anti-EphA2 polyclonal antibody (Santa Cruz). Expression of MT1-MMP was detected by western blotting with an anti-MT1-MMP monoclonal antibody (1D8).

The processed state of EphA2 of the cells into which the wild type EphA2 or processing-resistant EphA2 mutant had been introduced was detected by western blotting. As a result, the mutant deleted at a cleavage site showed resistance against processing by MT1-MMP (C). Phosphorylation of the EphA2 mutant with Ephrin-A1 was confirmed by immunoprecipitation with an EphA2 antibody (D).

5-2. Experiment Pulmonary Metastasis Experiment (FIGS. 5E to 5G)

Cells ($5\times10^6$/100 µl) were each administered to the tail vein of nude mice (BALB/c-nu). One month later, the mice were sacrificed and dissected to observe metastatic nodules of cancer cells formed in the lung. Observation of small metastatic lesions was made under a microscope after the lung tissue was HE-stained. The experiment was made using five mice and a T-test was used for statistical processing The mice administered with the cells into which the processing resistant EphA2 mutation had been introduced showed reduction in the formation of metastatic nodules in the lung (E, F). Further, the results of HE staining have showed that in the mice administered with the cells into which the processing resistant EphA2 mutation had been introduced, growth of cancer cells in the lung was significantly suppressed (G).

6-1. Detection of EphA2 Fragment in Carcinoma Tissue (FIGS. 6A and 6B)

Thin layer sections (5 µl) were cut from a frozen carcinoma tissue by using a cryostat and a tissue extract liquid was prepared using a RIPA buffer (100 μl/slide). An amount of protein extracted from each tissue was measured by CBB and EphA2 that expressed in each tissue, a fragment thereof, and MT1-MMP were analyzed by western blotting using a recognition antibody of the C terminal of EphA2 (Santa Cruz) and an MT1-MMP monoclonal antibody (1 D8). As a contrast, β-actin was detected simultaneously.

In the ovarian carcinoma tissue, only a low level of the full-length type EphA2 (intact) was detected and the fragment (EphA2 fragment) having a molecular weight of 60 kDa was the main (A, lower panel). An expression amount of MT1-MMP in these tissues was detected using an MT1-MMP monoclonal antibody (A, upper panel). The band attached with * was found without a primary antibody so that it was presumed to be a non-specific band (B). These results have suggested that even in the in vivo carcinoma tissue, EphA2 was processed by MT1-MMP and produced a 60-kDa fragment attributable to processing.

A similar experiment was made using the human head and neck carcinoma tissue and the results are shown in FIG. 8. Since an MT1-MMP expression was lower than that in the ovarian carcinoma, an EphA2 processing rate was very low (C, lower panel). The head and neck carcinoma tissue was analyzed by immunostaining. As a result, EphA2 expressed in a tumor portion and a non-tumor portion, while MT1-MMP showed a partial expression distribution in the tumor portion (A, B). These results have suggested that also in the head and neck carcinoma, processing of EphA2 similar to that in the ovarian carcinoma tissue occurred in tumor cells expressing MT1-MMP.

6-2. Immunohistological Analysis of N-Terminal and C-Terminal EphA2s and MT1-MMP (FIGS. 6C to 6F, and 8)

Localization of EphA2 and MT1-MMP in the ovarian carcinoma tissue was analyzed by a fluorescence immunohistological method. First, a frozen tissue section (4 μm) was treated with a 4% formalin/PBS buffer for 10 minutes at room temperature. After 5-min washing with PBS three times, the section was blocked with 0.2% goat serum/0.05% Triton-X100/PBS (for one hour at room temperature). Then, a primary antibody (anti-MT1-MMP polyclonal antibody (rabbit IgG, Merck)/anti-EphA2 N-terminal domain (mouse IgG, R&D), or a MT1-MMP polyclonal antibody/anti-EphA2 C-terminal domain (Santa Cruz) was subjected to overnight treatment at 4° C.

After the reaction, 5-min washing with PBS was performed three times, followed by treatment with anti-mouse IgG-Alexa 568 (Invitrogen) and anti-rabbit IgG-Alexa-488 (Invitrogen) (each, 1 μg/ml) at room temperature for one hour. After treatment with a DAPI-containing mounting medium (Vector Lab), observation was made under a fluorescence microscope. Localization of phosphorylated EphA2 was detected in a similar manner by using an anti-EphA2 phosphorylated tyr-594 polyclonal antibody (biorbyt limited), an anti-EphA2 phosphorylated ser-897 polyclonal antibody (Cell Application Inc), and an anti-MT1-MMP monoclonal antibody.

A positive stained site of MT1-MMP and a positive site of the C-terminal antibody of EphA2 (C) show co-localization. On the other hand, the positive stained site of the N-terminal antibody of EphA2 and that of MT1-MMP (D) do not show co-localization. This has suggested the possibility that many EphA2s that have highly expressed in the carcinoma tissue may be N-terminal cleaved studs. In the ovarian carcinoma tissue, expression of MT1-MMP and expression of ligand-independent phosphorylation of serine 897 residue of EphA2 showed co-localization (E). On the other hand, expression of MT1-MMP and expression of ligand-dependent phosphorylation of tyrosine 594 residue showed different localization (F).

The results of a similar experiment performed using the human and head carcinoma tissue are shown in FIG. 9. It shows the results of studying the phosphorylation kinetics of EphA2 at the MT1-MMP expression site by using two antibodies capable of recognizing phosphorylation of the intracellular domain of EphA2. Also in the head and neck carcinoma tissue, expression of MT1-MMP and expression of ligand-independent phosphorylation of serine 897 residue of EphA2 showed co-localization (A). On the other hand, expression of MT1-MMP and expression of ligand-dependent phosphorylation of tyrosine 594 residue showed different localization (B).

6-3. Immunostaining of N Terminal and C Terminal of EphA2 in Normal Ovarian Tissue and Ovarian Carcinoma Tissue (FIG. 11)

In a manner similar to that of 6-2, the normal ovarian tissue and the ovarian carcinoma tissue were stained with an anti-EphA2 N-terminal domain (mouse IgG, R&D) or an anti-EphA2 C-terminal domain (Santa Cruz). The results of the normal ovarian tissue are shown in FIG. 11A and the results of the ovarian carcinoma tissue are shown in FIG. 11B. As shown in FIG. 11, both the N terminal and the C terminal of EphA2 were detected from the normal carcinoma tissue and it has been confirmed that EphA2 was in an intact state. On the other hand, staining of the N terminal did not occur in the ovarian carcinoma tissue and it has therefore been confirmed that EphA2 lost the N terminal as a result of the processing.

6-4. Confirmation of Phosphorylation of EphA2 in Gastric Carcinoma Tissue and Colon Carcinoma Tissue (FIG. 12)

In a manner similar to that of 6-2, phosphorylation of EphA2 in the gastric carcinoma tissue and the colon carcinoma tissue was studied. After an anti-MT1-MMP mouse monoclonal antibody was bound to MT1-MMP, it was stained with a secondary antibody to which Alexa Fluor (registered trademark)-568 had been bound. After anti-EphA2 p-Ser$^{897}$ and anti-EphA2 p-Tyr$^{594}$ rabbit polyclonal antibodies were bound to EphA2 p-Ser$^{897}$ and EphA2 p-Tyr$^{594}$, respectively, they were stained with a secondary antibody to which Alexa Fluor (registered trademark)-488 had been bound.

The results of the gastric carcinoma tissue are shown in FIG. 12A and the results of the colon carcinoma tissue are shown in FIG. 12B. In both the gastric carcinoma tissue and the colon carcinoma tissue, expression of MT1-MMP and expression of EphA2 p-Ser$^{897}$ showed the same localization, but expression of MT1-MMP and expression of EphA2 p-Tyr$^{594}$ showed different localization (data were not shown).

This has strongly suggested that processing of EphA2 by MT1-MMP occurred similarly in various cancers.

6-5. Influence of MT1-MMP-Processing-Resistant EphA2 on Phenotype of Cancer Cells (FIG. 13)

In a manner similar to that of 5-1, MT1-MMP-processing-resistant EphA2 was expressed in A431 cells. The cells were seeded on a 10%-FCS-containing DMEM medium. Twenty four hours later, the morphology of the cells was observed under a microscope (200-fold).

The results are shown in FIG. 13. A431 cells have a spindle-like form peculiar to malignant cancer cells (refer to the results of Mock and normal EphA2 expression cells), while the cells expressing MT1-MMP-processing-resistant EphA2 changed to round shape (ucEphA2-CF-1 and ucEphA2-CF-2) like that of normal epithelial cells. This strongly suggests that ligand-dependent anti-tumor signaling is activated if cancer cells are not subjected to processing by MT1-MMP.

6-6. Confirmation of Production of EphA2 Fragment in A431 Cells (FIG. 14)

In a manner similar to that of 1, EphA2 was expressed in A431 cells and a fragment cleaved by endogenous MT1-MMP was detected by Western blotting. An antibody employed has an epitope in the cysteine rich domain of the EphA2 protein. Two bands were observed presumably because EphA2 was cleaved at a site in addition to the site confirmed by the present inventors.

SEQUENCE LISTING FREE TEXT

SEQ ID NO: 1 to 4 show an amino acid sequence of an EphA2 fragment to be used for the testing method of the present invention.

SEQ ID NO: 5 shows a full-length amino acid sequence of EphA2.

SEQ ID NO: 6 and 7 show the sequence of siRNA#1.

SEQ ID NO: 8 and 9 show the sequence of siRNA#2.

SEQ ID NO: 10 and 11 show the sequence of siRNA#3.

The invention claimed is:

1. A method of diagnosing and treating a subject suffering from cancer, comprising:
   (a) obtaining a sample from the subject;
   (b) detecting a fragment of EphA2 protein having a molecular weight of from 30 kDa to 80 kDa in the sample, wherein the fragment is obtained as a result of cleavage between S431 and V432 or between I434 and N435 of SEQ ID NO: 5;
   (c) distinguishing the fragment in step (b) from full length EphA2;
   (d) diagnosing the subject with cancer when the presence of the fragment of EphA2 protein is detected; and
   (e) administering an effective amount of a treatment for cancer to the diagnosed subject.

2. The method according to claim 1, wherein the cancer is an EphA2-expressing cancer.

3. The method according to claim 1, wherein the sample is at least one selected from blood, lymph, urine, and feces.

4. The method according to claim 1, wherein the fragment of EphA2 protein is detected using an antibody capable of recognizing the EphA2 fragment.

* * * * *

SEQUENCE LISTING

```
<160> NUMBER OF SEQ ID NOS: 11

<210> SEQ ID NO 1
<211> LENGTH: 431
<212> TYPE: PRT
<213> ORGANISM: Homo sapiens

<400> SEQUENCE: 1

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285
```

```
Pro Cys Leu Glu Cys Pro Glu His Thr Leu Pro Ser Pro Glu Gly Ala
    290                 295                 300

Thr Ser Cys Glu Cys Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser
            420                 425                 430

<210> SEQ ID NO 2
<211> LENGTH: 545
<212> TYPE: PRT
<213> ORGANISM: Homo sapiens

<400> SEQUENCE: 2

Val Ser Ile Asn Gln Thr Glu Pro Pro Lys Val Arg Leu Glu Gly Arg
1               5                   10                  15

Ser Thr Thr Ser Leu Ser Val Ser Trp Ser Ile Pro Pro Gln Gln
            20                  25                  30

Ser Arg Val Trp Lys Tyr Glu Val Thr Tyr Arg Lys Lys Gly Asp Ser
        35                  40                  45

Asn Ser Tyr Asn Val Arg Arg Thr Glu Gly Phe Ser Val Thr Leu Asp
    50                  55                  60

Asp Leu Ala Pro Asp Thr Thr Tyr Leu Val Gln Val Gln Ala Leu Thr
65                  70                  75                  80

Gln Glu Gly Gln Gly Ala Gly Ser Lys Val His Glu Phe Gln Thr Leu
                85                  90                  95

Ser Pro Glu Gly Ser Gly Asn Leu Ala Val Ile Gly Val Ala Val
            100                 105                 110

Gly Val Val Leu Leu Leu Val Leu Ala Gly Val Gly Phe Phe Ile His
        115                 120                 125

Arg Arg Arg Lys Asn Gln Arg Ala Arg Gln Ser Pro Glu Asp Val Tyr
    130                 135                 140

Phe Ser Lys Ser Glu Gln Leu Lys Pro Leu Lys Thr Tyr Val Asp Pro
145                 150                 155                 160

His Thr Tyr Glu Asp Pro Asn Gln Ala Val Leu Lys Phe Thr Thr Glu
                165                 170                 175

Ile His Pro Ser Cys Val Thr Arg Gln Lys Val Ile Gly Ala Gly Glu
            180                 185                 190

Phe Gly Glu Val Tyr Lys Gly Met Leu Lys Thr Ser Ser Gly Lys Lys
        195                 200                 205

Glu Val Pro Val Ala Ile Lys Thr Leu Lys Ala Gly Tyr Thr Glu Lys
    210                 215                 220

Gln Arg Val Asp Phe Leu Gly Glu Ala Gly Ile Met Gly Gln Phe Ser
```

```
                225                 230                 235                 240
        His His Asn Ile Ile Arg Leu Glu Gly Val Ile Ser Lys Tyr Lys Pro
                            245                 250                 255

Met Met Ile Ile Thr Glu Tyr Met Glu Asn Gly Ala Leu Asp Lys Phe
                            260                 265                 270

Leu Arg Glu Lys Asp Gly Glu Phe Ser Val Leu Gln Leu Val Gly Met
                            275                 280                 285

Leu Arg Gly Ile Ala Ala Gly Met Lys Tyr Leu Ala Asn Met Asn Tyr
                            290                 295                 300

Val His Arg Asp Leu Ala Ala Arg Asn Ile Leu Val Asn Ser Asn Leu
        305                 310                 315                 320

Val Cys Lys Val Ser Asp Phe Gly Leu Ser Arg Val Leu Glu Asp Asp
                            325                 330                 335

Pro Glu Ala Thr Tyr Thr Thr Ser Gly Gly Lys Ile Pro Ile Arg Trp
                            340                 345                 350

Thr Ala Pro Glu Ala Ile Ser Tyr Arg Lys Phe Thr Ser Ala Ser Asp
                            355                 360                 365

Val Trp Ser Phe Gly Ile Val Met Trp Glu Val Met Thr Tyr Gly Glu
                            370                 375                 380

Arg Pro Tyr Trp Glu Leu Ser Asn His Glu Val Met Lys Ala Ile Asn
        385                 390                 395                 400

Asp Gly Phe Arg Leu Pro Thr Pro Met Asp Cys Pro Ser Ala Ile Tyr
                            405                 410                 415

Gln Leu Met Met Gln Cys Trp Gln Glu Arg Ala Arg Pro Lys
                            420                 425                 430

Phe Ala Asp Ile Val Ser Ile Leu Asp Lys Leu Ile Arg Ala Pro Asp
                            435                 440                 445

Ser Leu Lys Thr Leu Ala Asp Phe Asp Pro Arg Val Ser Ile Arg Leu
                            450                 455                 460

Pro Ser Thr Ser Gly Ser Glu Gly Val Pro Phe Arg Thr Val Ser Glu
        465                 470                 475                 480

Trp Leu Glu Ser Ile Lys Met Gln Gln Tyr Thr Glu His Phe Met Ala
                            485                 490                 495

Ala Gly Tyr Thr Ala Ile Glu Lys Val Val Gln Met Thr Asn Asp Asp
                            500                 505                 510

Ile Lys Arg Ile Gly Val Arg Leu Pro Gly His Gln Lys Arg Ile Ala
                            515                 520                 525

Tyr Ser Leu Leu Gly Leu Lys Asp Gln Val Asn Thr Val Gly Ile Pro
        530                 535                 540

Ile
        545

<210> SEQ ID NO 3
<211> LENGTH: 434
<212> TYPE: PRT
<213> ORGANISM: Homo sapiens

<400> SEQUENCE: 3

Met Glu Leu Gln Ala Ala Arg Ala Cys Phe Ala Leu Leu Trp Gly Cys
        1                   5                   10                  15

Ala Leu Ala Ala Ala Ala Ala Ala Gln Gly Lys Glu Val Val Leu Leu
                            20                  25                  30

Asp Phe Ala Ala Ala Gly Gly Glu Leu Gly Trp Leu Thr His Pro Tyr
                            35                  40                  45
```

Gly Lys Gly Trp Asp Leu Met Gln Asn Ile Met Asn Asp Met Pro Ile
 50                  55                  60
Tyr Met Tyr Ser Val Cys Asn Val Met Ser Gly Asp Gln Asp Asn Trp
 65                  70                  75                  80
Leu Arg Thr Asn Trp Val Tyr Arg Gly Glu Ala Glu Arg Ile Phe Ile
                 85                  90                  95
Glu Leu Lys Phe Thr Val Arg Asp Cys Asn Ser Phe Pro Gly Gly Ala
            100                 105                 110
Ser Ser Cys Lys Glu Thr Phe Asn Leu Tyr Tyr Ala Glu Ser Asp Leu
        115                 120                 125
Asp Tyr Gly Thr Asn Phe Gln Lys Arg Leu Phe Thr Lys Ile Asp Thr
130                 135                 140
Ile Ala Pro Asp Glu Ile Thr Val Ser Ser Asp Phe Glu Ala Arg His
145                 150                 155                 160
Val Lys Leu Asn Val Glu Arg Ser Val Gly Pro Leu Thr Arg Lys
                165                 170                 175
Gly Phe Tyr Leu Ala Phe Gln Asp Ile Gly Ala Cys Val Ala Leu Leu
            180                 185                 190
Ser Val Arg Val Tyr Tyr Lys Lys Cys Pro Glu Leu Leu Gln Gly Leu
        195                 200                 205
Ala His Phe Pro Glu Thr Ile Ala Gly Ser Asp Ala Pro Ser Leu Ala
210                 215                 220
Thr Val Ala Gly Thr Cys Val Asp His Ala Val Pro Pro Gly Gly
225                 230                 235                 240
Glu Glu Pro Arg Met His Cys Ala Val Asp Gly Glu Trp Leu Val Pro
                245                 250                 255
Ile Gly Gln Cys Leu Cys Gln Ala Gly Tyr Glu Lys Val Glu Asp Ala
            260                 265                 270
Cys Gln Ala Cys Ser Pro Gly Phe Phe Lys Phe Glu Ala Ser Glu Ser
        275                 280                 285
Pro Cys Leu Glu Cys Pro Glu His Thr Leu Pro Ser Pro Glu Gly Ala
290                 295                 300
Thr Ser Cys Glu Cys Glu Glu Gly Phe Phe Arg Ala Pro Gln Asp Pro
305                 310                 315                 320
Ala Ser Met Pro Cys Thr Arg Pro Pro Ser Ala Pro His Tyr Leu Thr
                325                 330                 335
Ala Val Gly Met Gly Ala Lys Val Glu Leu Arg Trp Thr Pro Pro Gln
            340                 345                 350
Asp Ser Gly Gly Arg Glu Asp Ile Val Tyr Ser Val Thr Cys Glu Gln
        355                 360                 365
Cys Trp Pro Glu Ser Gly Glu Cys Gly Pro Cys Glu Ala Ser Val Arg
370                 375                 380
Tyr Ser Glu Pro Pro His Gly Leu Thr Arg Thr Ser Val Thr Val Ser
385                 390                 395                 400
Asp Leu Glu Pro His Met Asn Tyr Thr Phe Thr Val Glu Ala Arg Asn
                405                 410                 415
Gly Val Ser Gly Leu Val Thr Ser Arg Ser Phe Arg Thr Ala Ser Val
            420                 425                 430
Ser Ile

<210> SEQ ID NO 4
<211> LENGTH: 542
<212> TYPE: PRT
<213> ORGANISM: Homo sapiens

<400> SEQUENCE: 4

```
Asn Gln Thr Glu Pro Pro Lys Val Arg Leu Glu Gly Arg Ser Thr Thr
1               5                   10                  15

Ser Leu Ser Val Ser Trp Ser Ile Pro Pro Gln Gln Ser Arg Val
            20                  25                  30

Trp Lys Tyr Glu Val Thr Tyr Arg Lys Lys Gly Asp Ser Asn Ser Tyr
            35                  40                  45

Asn Val Arg Arg Thr Glu Gly Phe Ser Val Thr Leu Asp Asp Leu Ala
        50                  55                  60

Pro Asp Thr Thr Tyr Leu Val Gln Val Gln Ala Leu Thr Gln Glu Gly
65                  70                  75                  80

Gln Gly Ala Gly Ser Lys Val His Glu Phe Gln Thr Leu Ser Pro Glu
                85                  90                  95

Gly Ser Gly Asn Leu Ala Val Ile Gly Val Ala Val Gly Val Val
            100                 105                 110

Leu Leu Leu Val Leu Ala Gly Val Gly Phe Phe Ile His Arg Arg Arg
            115                 120                 125

Lys Asn Gln Arg Ala Arg Gln Ser Pro Glu Asp Val Tyr Phe Ser Lys
    130                 135                 140

Ser Glu Gln Leu Lys Pro Leu Lys Thr Tyr Val Asp Pro His Thr Tyr
145                 150                 155                 160

Glu Asp Pro Asn Gln Ala Val Leu Lys Phe Thr Thr Glu Ile His Pro
                165                 170                 175

Ser Cys Val Thr Arg Gln Lys Val Ile Gly Ala Gly Glu Phe Gly Glu
            180                 185                 190

Val Tyr Lys Gly Met Leu Lys Thr Ser Ser Gly Lys Lys Glu Val Pro
        195                 200                 205

Val Ala Ile Lys Thr Leu Lys Ala Gly Tyr Thr Glu Lys Gln Arg Val
    210                 215                 220

Asp Phe Leu Gly Glu Ala Gly Ile Met Gly Gln Phe Ser His His Asn
225                 230                 235                 240

Ile Ile Arg Leu Glu Gly Val Ile Ser Lys Tyr Lys Pro Met Met Ile
                245                 250                 255

Ile Thr Glu Tyr Met Glu Asn Gly Ala Leu Asp Lys Phe Leu Arg Glu
            260                 265                 270

Lys Asp Gly Glu Phe Ser Val Leu Gln Leu Val Gly Met Leu Arg Gly
        275                 280                 285

Ile Ala Ala Gly Met Lys Tyr Leu Ala Asn Met Asn Tyr Val His Arg
    290                 295                 300

Asp Leu Ala Ala Arg Asn Ile Leu Val Asn Ser Asn Leu Val Cys Lys
305                 310                 315                 320

Val Ser Asp Phe Gly Leu Ser Arg Val Leu Glu Asp Asp Pro Glu Ala
                325                 330                 335

Thr Tyr Thr Thr Ser Gly Gly Lys Ile Pro Ile Arg Trp Thr Ala Pro
            340                 345                 350

Glu Ala Ile Ser Tyr Arg Lys Phe Thr Ser Ala Ser Asp Val Trp Ser
        355                 360                 365

Phe Gly Ile Val Met Trp Glu Val Met Thr Tyr Gly Glu Arg Pro Tyr
    370                 375                 380

Trp Glu Leu Ser Asn His Glu Val Met Lys Ala Ile Asn Asp Gly Phe
385                 390                 395                 400

Arg Leu Pro Thr Pro Met Asp Cys Pro Ser Ala Ile Tyr Gln Leu Met
```

```
            405                 410                 415
Met Gln Cys Trp Gln Gln Glu Arg Ala Arg Arg Pro Lys Phe Ala Asp
            420                 425                 430

Ile Val Ser Ile Leu Asp Lys Leu Ile Arg Ala Pro Asp Ser Leu Lys
            435                 440                 445

Thr Leu Ala Asp Phe Asp Pro Arg Val Ser Ile Arg Leu Pro Ser Thr
450                 455                 460

Ser Gly Ser Glu Gly Val Pro Phe Arg Thr Val Ser Glu Trp Leu Glu
465                 470                 475                 480

Ser Ile Lys Met Gln Gln Tyr Thr Glu His Phe Met Ala Ala Gly Tyr
            485                 490                 495

Thr Ala Ile Glu Lys Val Val Gln Met Thr Asn Asp Asp Ile Lys Arg
            500                 505                 510

Ile Gly Val Arg Leu Pro Gly His Gln Lys Arg Ile Ala Tyr Ser Leu
            515                 520                 525

Leu Gly Leu Lys Asp Gln Val Asn Thr Val Gly Ile Pro Ile
530                 535                 540

<210> SEQ ID NO 5
<211> LENGTH: 976
<212> TYPE: PRT
<213> ORGANISM: Homo sapiens

<400> SEQUENCE: 5

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
        50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
        130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
            195                 200                 205

Ala His Phe Pro Glu Thr Ile Ala Gly Ser Asp Ala Pro Ser Leu Ala
        210                 215                 220

Thr Val Ala Gly Thr Cys Val Asp His Ala Val Val Pro Pro Gly Gly
225                 230                 235                 240
```

-continued

```
Glu Glu Pro Arg Met His Cys Ala Val Asp Gly Glu Trp Leu Val Pro
            245                 250                 255
Ile Gly Gln Cys Leu Cys Gln Ala Gly Tyr Glu Lys Val Glu Asp Ala
            260                 265                 270
Cys Gln Ala Cys Ser Pro Gly Phe Phe Lys Phe Glu Ala Ser Glu Ser
            275                 280                 285
Pro Cys Leu Glu Cys Pro Glu His Thr Leu Pro Ser Pro Glu Gly Ala
            290                 295                 300
Thr Ser Cys Glu Cys Glu Gly Phe Phe Arg Ala Pro Gln Asp Pro
305                 310                 315                 320
Ala Ser Met Pro Cys Thr Arg Pro Pro Ser Ala Pro His Tyr Leu Thr
            325                 330                 335
Ala Val Gly Met Gly Ala Lys Val Glu Leu Arg Trp Thr Pro Pro Gln
            340                 345                 350
Asp Ser Gly Gly Arg Glu Asp Ile Val Tyr Ser Val Thr Cys Glu Gln
            355                 360                 365
Cys Trp Pro Glu Ser Gly Glu Cys Gly Pro Cys Glu Ala Ser Val Arg
            370                 375                 380
Tyr Ser Glu Pro Pro His Gly Leu Thr Arg Thr Ser Val Thr Val Ser
385                 390                 395                 400
Asp Leu Glu Pro His Met Asn Tyr Thr Phe Thr Val Glu Ala Arg Asn
            405                 410                 415
Gly Val Ser Gly Leu Val Thr Ser Arg Ser Phe Arg Thr Ala Ser Val
            420                 425                 430
Ser Ile Asn Gln Thr Glu Pro Pro Lys Val Arg Leu Glu Gly Arg Ser
            435                 440                 445
Thr Thr Ser Leu Ser Val Ser Trp Ser Ile Pro Pro Pro Gln Gln Ser
            450                 455                 460
Arg Val Trp Lys Tyr Glu Val Thr Tyr Arg Lys Lys Gly Asp Ser Asn
465                 470                 475                 480
Ser Tyr Asn Val Arg Arg Thr Glu Gly Phe Ser Val Thr Leu Asp Asp
            485                 490                 495
Leu Ala Pro Asp Thr Thr Tyr Leu Val Gln Val Gln Ala Leu Thr Gln
            500                 505                 510
Glu Gly Gln Gly Ala Gly Ser Lys Val His Glu Phe Gln Thr Leu Ser
            515                 520                 525
Pro Glu Gly Ser Gly Asn Leu Ala Val Ile Gly Gly Val Ala Val Gly
            530                 535                 540
Val Val Leu Leu Leu Val Leu Ala Gly Val Gly Phe Phe Ile His Arg
545                 550                 555                 560
Arg Arg Lys Asn Gln Arg Ala Arg Gln Ser Pro Glu Asp Val Tyr Phe
            565                 570                 575
Ser Lys Ser Glu Gln Leu Lys Pro Leu Lys Thr Tyr Val Asp Pro His
            580                 585                 590
Thr Tyr Glu Asp Pro Asn Gln Ala Val Leu Lys Phe Thr Thr Glu Ile
            595                 600                 605
His Pro Ser Cys Val Thr Arg Gln Lys Val Ile Gly Ala Gly Glu Phe
            610                 615                 620
Gly Glu Val Tyr Lys Gly Met Leu Lys Thr Ser Ser Gly Lys Lys Glu
625                 630                 635                 640
Val Pro Val Ala Ile Lys Thr Leu Lys Ala Gly Tyr Thr Glu Lys Gln
            645                 650                 655
Arg Val Asp Phe Leu Gly Glu Ala Gly Ile Met Gly Gln Phe Ser His
```

```
                    660                 665                 670
His Asn Ile Ile Arg Leu Glu Gly Val Ile Ser Lys Tyr Lys Pro Met
                675                 680                 685

Met Ile Ile Thr Glu Tyr Met Glu Asn Gly Ala Leu Asp Lys Phe Leu
            690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
                755                 760                 765

Glu Ala Thr Tyr Thr Thr Ser Gly Gly Lys Ile Pro Ile Arg Trp Thr
            770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
                820                 825                 830

Gly Phe Arg Leu Pro Thr Pro Met Asp Cys Pro Ser Ala Ile Tyr Gln
                835                 840                 845

Leu Met Met Gln Cys Trp Gln Gln Glu Arg Ala Arg Arg Pro Lys Phe
            850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
                915                 920                 925

Gly Tyr Thr Ala Ile Glu Lys Val Val Gln Met Thr Asn Asp Asp Ile
            930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 6
<211> LENGTH: 21
<212> TYPE: DNA
<213> ORGANISM: artificial
<220> FEATURE:
<223> OTHER INFORMATION: Sense sequence of siRNA #1.

<400> SEQUENCE: 6
ggauggacac ggagaauuut t                                              21

<210> SEQ ID NO 7
<211> LENGTH: 21
<212> TYPE: DNA
<213> ORGANISM: artificial
<220> FEATURE:
<223> OTHER INFORMATION: Antisense sequence of siRNA #1.
```

```
<400> SEQUENCE: 7
aaauucuccg uguccaucct t                                              21

<210> SEQ ID NO 8
<211> LENGTH: 21
<212> TYPE: DNA
<213> ORGANISM: artificial
<220> FEATURE:
<223> OTHER INFORMATION: Sense sequence of siRNA #2.

<400> SEQUENCE: 8
gcgaugaagu cuucacuuat t                                              21

<210> SEQ ID NO 9
<211> LENGTH: 21
<212> TYPE: DNA
<213> ORGANISM: artificial
<220> FEATURE:
<223> OTHER INFORMATION: Antisense sequence of siRNA #2.

<400> SEQUENCE: 9
uaagugaaga cuucaucgct t                                              21

<210> SEQ ID NO 10
<211> LENGTH: 21
<212> TYPE: DNA
<213> ORGANISM: artificial
<220> FEATURE:
<223> OTHER INFORMATION: Sense sequence of siRNA #3.

<400> SEQUENCE: 10
ggguagagac ccugagacat t                                              21

<210> SEQ ID NO 11
<211> LENGTH: 21
<212> TYPE: DNA
<213> ORGANISM: artificial
<220> FEATURE:
<223> OTHER INFORMATION: Antisense sequence of siRNA #3.

<400> SEQUENCE: 11
ugucucaggg ucucuaccct t                                              21
```